(12) United States Patent
Akella et al.

(10) Patent No.: US 12,093,022 B2
(45) Date of Patent: Sep. 17, 2024

(54) SYSTEMS AND METHODS FOR AUTOMATIC JOB ASSIGNMENT

(71) Applicant: R4N63R Capital LLC, Wilmington, DE (US)

(72) Inventors: Prasad Narasimha Akella, Palo Alto, CA (US); Ananth Uggirala, Mountain View, CA (US); Krishnendu Chaudhury, Saratoga, CA (US); Sameer Gupta, Palo Alto, CA (US); Sujay Venkata Krishna Narumanchi, Bangalore (IN)

(73) Assignee: R4N63R CAPITAL LLC, Wilmington, DE (US)

( * ) Notice: Subject to any disclaimer, the term of this patent is extended or adjusted under 35 U.S.C. 154(b) by 214 days.

(21) Appl. No.: 16/181,191

(22) Filed: Nov. 5, 2018

(65) Prior Publication Data
US 2019/0138973 A1   May 9, 2019

Related U.S. Application Data

(60) Provisional application No. 62/581,541, filed on Nov. 3, 2017.

(51) Int. Cl.
*G05B 19/418* (2006.01)
*G06F 9/448* (2018.01)
(Continued)

(52) U.S. Cl.
CPC ... *G05B 19/4183* (2013.01); *G05B 19/41835* (2013.01); *G06F 9/4498* (2018.02);
(Continued)

(58) Field of Classification Search
CPC ........ G06N 20/00; G06N 3/008; G06N 3/006; G06N 7/01; G06K 9/00335;
(Continued)

(56) References Cited

U.S. PATENT DOCUMENTS 6,963,827 B1  11/2005  Elyea et al.
7,401,728 B2   7/2008  Markham et al.
(Continued)

FOREIGN PATENT DOCUMENTS

CN  106094707 A  11/2016
CN  107066979 A   8/2017
(Continued)

OTHER PUBLICATIONS

Sepp Hochreiter & Jurgen Schmidhuber, *Long Short-Term memory*, Neural Computation, vol. 9, Issue 8, p. 1735-1780, Nov. 15, 1997.
(Continued)

*Primary Examiner* — Mehmet Yesildag
*Assistant Examiner* — Ayanna Minor
(74) *Attorney, Agent, or Firm* — Dorsey & Whitney LLP

(57) ABSTRACT

Embodiments of the present invention provide a machine and continuous data set including process data, quality data, specific actor data, and ergonomic data (among others) to create more accurate job assignments that maximize efficiency, quality and worker safety. Using the data set, tasks may be assigned to actors based on objective statistical data such as skills, task requirements, ergonomics and time availability. Assigning tasks in this way can provide unique value for manufacturers who currently conduct similar analyses using only minimal observational data.

22 Claims, 18 Drawing Sheets

(51) Int. Cl.

| | | |
|---|---|---|
| G06F 9/48 | (2006.01) | |
| G06F 11/07 | (2006.01) | |
| G06F 11/34 | (2006.01) | |
| G06F 16/22 | (2019.01) | |
| G06F 16/23 | (2019.01) | |
| G06F 16/2455 | (2019.01) | |
| G06F 16/901 | (2019.01) | |
| G06F 16/9035 | (2019.01) | |
| G06F 16/904 | (2019.01) | |
| G06F 30/20 | (2020.01) | |
| G06F 30/23 | (2020.01) | |
| G06F 30/27 | (2020.01) | |
| G06N 3/008 | (2023.01) | |
| G06N 3/04 | (2023.01) | |
| G06N 3/044 | (2023.01) | |
| G06N 3/045 | (2023.01) | |
| G06N 3/08 | (2023.01) | |
| G06N 3/084 | (2023.01) | |
| G06N 7/01 | (2023.01) | |
| G06N 20/00 | (2019.01) | |
| G06Q 10/06 | (2023.01) | |
| G06Q 10/0631 | (2023.01) | |
| G06Q 10/0639 | (2023.01) | |
| G06T 19/00 | (2011.01) | |
| G06V 10/25 | (2022.01) | |
| G06V 10/44 | (2022.01) | |
| G06V 10/82 | (2022.01) | |
| G06V 20/52 | (2022.01) | |
| G06V 40/20 | (2022.01) | |
| G09B 19/00 | (2006.01) | |
| B25J 9/16 | (2006.01) | |
| G01M 99/00 | (2011.01) | |
| G05B 19/423 | (2006.01) | |
| G05B 23/02 | (2006.01) | |
| G06F 18/21 | (2023.01) | |
| G06F 111/10 | (2020.01) | |
| G06F 111/20 | (2020.01) | |
| G06N 3/006 | (2023.01) | |
| G06Q 10/083 | (2023.01) | |
| G06Q 50/26 | (2012.01) | |
| G16H 10/60 | (2018.01) | |

(52) U.S. Cl.
CPC ........ *G06F 9/4881* (2013.01); *G06F 11/0721* (2013.01); *G06F 11/079* (2013.01); *G06F 11/3452* (2013.01); *G06F 16/2228* (2019.01); *G06F 16/2365* (2019.01); *G06F 16/24568* (2019.01); *G06F 16/9024* (2019.01); *G06F 16/9035* (2019.01); *G06F 16/904* (2019.01); *G06F 30/20* (2020.01); *G06F 30/23* (2020.01); *G06F 30/27* (2020.01); *G06N 3/008* (2013.01); *G06N 3/04* (2013.01); *G06N 3/044* (2023.01); *G06N 3/045* (2023.01); *G06N 3/08* (2013.01); *G06N 3/084* (2013.01); *G06N 7/01* (2023.01); *G06N 20/00* (2019.01); *G06Q 10/06* (2013.01); *G06Q 10/063112* (2013.01); *G06Q 10/06316* (2013.01); *G06Q 10/06393* (2013.01); *G06Q 10/06395* (2013.01); *G06Q 10/06398* (2013.01); *G06T 19/006* (2013.01); *G06V 10/25* (2022.01); *G06V 10/454* (2022.01); *G06V 10/82* (2022.01); *G06V 20/52* (2022.01); *G06V 40/20* (2022.01); *G09B 19/00* (2013.01); *B25J 9/1664* (2013.01); *B25J 9/1697* (2013.01); *G01M 99/005* (2013.01); *G05B 19/41865* (2013.01); *G05B 19/423* (2013.01); *G05B 23/0224* (2013.01); *G05B 2219/32056* (2013.01); *G05B 2219/36442* (2013.01); *G06F 18/217* (2023.01); *G06F 2111/10* (2020.01); *G06F 2111/20* (2020.01); *G06N 3/006* (2013.01); *G06Q 10/083* (2013.01); *G06Q 50/26* (2013.01); *G16H 10/60* (2018.01)

(58) Field of Classification Search
CPC .. G06K 9/00624; G06K 9/4604; G06Q 10/06; G06Q 10/083; G06Q 50/26; G05B 19/00; G05B 19/423; G05B 23/0224; G05B 2219/36442; G05B 2219/32056; G06F 16/24568; G06F 11/3452; G06F 9/4881; G06F 9/4498; G06F 2111/10; G06F 2111/20; G06F 18/217; G06V 40/20; G06V 10/25; G06V 10/82; G06V 10/454; G06V 20/52; G06T 19/006; G01M 99/005; G16H 10/60
See application file for complete search history.

(56) References Cited

U.S. PATENT DOCUMENTS

| | | | |
|---|---|---|---|
| 8,260,783 | B2 | 9/2012 | Milam |
| 8,306,931 | B1 | 11/2012 | Bowman et al. |
| 9,305,216 | B1* | 4/2016 | Mishra ................ G06F 16/583 |
| 9,471,610 | B1 | 10/2016 | Long et al. |
| 9,921,726 | B1 | 3/2018 | Sculley et al. |
| 10,445,702 | B1 | 10/2019 | Hunt |
| 10,713,794 | B1* | 7/2020 | He ........................ G06N 3/084 |
| 10,852,712 | B2 | 12/2020 | Ben-Bassat et al. |
| 11,226,720 | B1 | 1/2022 | Vandivere et al. |
| 2003/0229471 | A1 | 12/2003 | Guralnik et al. |
| 2005/0105765 | A1 | 5/2005 | Han et al. |
| 2006/0224254 | A1 | 10/2006 | Rumi et al. |
| 2006/0241792 | A1 | 10/2006 | Pretlove et al. |
| 2006/0271526 | A1 | 11/2006 | Charnock et al. |
| 2009/0016599 | A1 | 1/2009 | Eaton et al. |
| 2009/0016600 | A1 | 1/2009 | Eaton et al. |
| 2009/0089227 | A1 | 4/2009 | Sturrock et al. |
| 2010/0082512 | A1 | 4/2010 | Myerson et al. |
| 2011/0043626 | A1 | 2/2011 | Cobb et al. |
| 2012/0197898 | A1 | 8/2012 | Pandey et al. |
| 2012/0225413 | A1 | 9/2012 | Kotranza et al. |
| 2013/0234854 | A1 | 9/2013 | Mukherjee et al. |
| 2013/0307693 | A1 | 11/2013 | Stone et al. |
| 2013/0339923 | A1 | 12/2013 | Xu et al. |
| 2014/0003710 | A1 | 1/2014 | Seow et al. |
| 2014/0079297 | A1 | 3/2014 | Tadayon et al. |
| 2014/0172357 | A1 | 6/2014 | Heinonen |
| 2014/0222813 | A1 | 8/2014 | Yang et al. |
| 2014/0275888 | A1 | 9/2014 | Wegerich et al. |
| 2014/0277593 | A1* | 9/2014 | Nixon ................ G06F 3/04842 700/11 |
| 2014/0279776 | A1 | 9/2014 | Brown et al. |
| 2014/0326084 | A1 | 11/2014 | Bhushan |
| 2014/0337000 | A1 | 11/2014 | Asenjo et al. |
| 2014/0379156 | A1 | 12/2014 | Kamel et al. |
| 2015/0110388 | A1 | 4/2015 | Eaton et al. |
| 2015/0363438 | A1 | 12/2015 | Botelho |
| 2015/0363741 | A1* | 12/2015 | Chandra .......... G06Q 10/06311 705/7.17 |
| 2015/0364158 | A1 | 12/2015 | Gupte et al. |
| 2016/0085607 | A1 | 3/2016 | Marr et al. |
| 2016/0322078 | A1 | 11/2016 | Bose et al. |
| 2016/0375524 | A1 | 12/2016 | Hsu |
| 2017/0098161 | A1 | 4/2017 | Ellenbogen et al. |
| 2017/0232613 | A1 | 8/2017 | Ponulak et al. |
| 2017/0243154 | A1 | 8/2017 | Fletter et al. |
| 2017/0245806 | A1* | 8/2017 | Elhawary ............ A61B 5/1122 |
| 2017/0262697 | A1 | 9/2017 | Kaps et al. |
| 2017/0308800 | A1 | 10/2017 | Cichon et al. |
| 2017/0320102 | A1 | 11/2017 | McVaugh et al. |

(56) References Cited

U.S. PATENT DOCUMENTS

| | | | |
|---|---|---|---|
| 2018/0011973 | A1 | 1/2018 | Fish et al. |
| 2018/0039745 | A1* | 2/2018 | Chevalier ............... G16H 30/40 |
| 2018/0056520 | A1* | 3/2018 | Ozaki .................... B25J 13/084 |
| 2018/0059630 | A1 | 3/2018 | Yang et al. |
| 2018/0139309 | A1 | 5/2018 | Pasam et al. |
| 2018/0324199 | A1 | 11/2018 | Crotinger et al. |
| 2018/0330250 | A1 | 11/2018 | Nakayama et al. |
| 2018/0330287 | A1 | 11/2018 | Tripathi |
| 2019/0034734 | A1* | 1/2019 | Yen ..................... G06F 18/2413 |
| 2019/0058719 | A1 | 2/2019 | Kar et al. |
| 2019/0138971 | A1 | 5/2019 | Uggirala et al. |
| 2019/0320898 | A1 | 10/2019 | Dirghangi et al. |
| 2020/0051203 | A1 | 2/2020 | Nurvitadhi et al. |
| 2020/0128307 | A1 | 4/2020 | Li |
| 2020/0293972 | A1 | 9/2020 | Arao et al. |

FOREIGN PATENT DOCUMENTS

| | | |
|---|---|---|
| EP | 2626757 | 8/2013 |
| EP | 2996006 A1 | 3/2016 |
| WO | WO2012141601 | 10/2012 |
| WO | 2017-040167 | 3/2017 |
| WO | 2017091883 A1 | 6/2017 |
| WO | 2018009405 A1 | 1/2018 |

OTHER PUBLICATIONS

Matthew Zeiler & Rob Fergus, Visualizing and Understanding Convolution Networks, arXiv;1311.2901v3, Nov. 28, 2013, pp. 11.

Ross Girshick, *Fast R-CNN*, Proceedings of the 2015 IEEE International Conference on Computer Vision (ICCV), p. 1440-1448, Dec. 7-13, 2015.

Shaoqing Ren et al., *Faster R-CNN: Towards Real Time Object Detection with Region Proposal Networks*, Proceedings of the 28th International Conference on Neural Information Processing Systems, vol. 1, p. 91-99, Dec. 7-12, 2015.

Christian Szegedy et al., *Inception-v4, Inception-Resnet and the Impact of Residual Connections on Learning*, ICLR 2016 Workshop, Feb. 18, 2016.

Jonathan Huang et al., *Speed/Accuracy Trade-Offs for Modern Convolutional Object Detectors*, Proceedings of the 2017 IEEE Conference on Computer Vision and Pattern Recognition (CVPR), Nov. 9, 2017.

Chen, L., et al., "Sensor-Based Activity Recognition", in IEEE Transactions on Systems, Man, and Cybernetics, Part C (Applications and Reviews), vol. 42, No. 6, doi: 10.1109/TSMCC.2012.2198883, Nov. 2012, pp. 790-808.

Ko, T., "A Survey on Behavior Analysis in Video Surveillance for Homeland Security Applications", 2008 37th IEEE Applied Imagery Pattern Recognition Workshop, Washington, DC, USA, doi: 10.1109/AIPR.2008/4906450, 2008, pp. 1-8.

Grinciunaite, et al., "Human Pose Estimation in Space and Time Using 3d cnn", European Conference on Computer Vision. Cham: Springer International Publishing, 2016. (Year:2016).

Zhang, et al., "Probabilistic Graphlet Transfer for Photo Cropping", IEEE Transactions on Image Processing 22.2 (2012):802-815 (Year: 2012).

Ji, et al., "3D Convolutional Neural Networks for Human Action Recognition", IEEE Transactions on Pattern Analysis and Machine Intelligence 35.1 (2012): 221-231. (Year: 2012).

* cited by examiner

JOB ASSIGNMENT - OUTPUT

| Associate | Assigned Station | Skill Fit | Recent Fit | Experience Fit | |
|---|---|---|---|---|---|
| Mary | Station 6 | ● Good | ● Good | ● Bad | ● Not enough |
| Max | Station 4 | ● Good | ● Good | ● Good | ● Good |
| Jill | Station 7 | ● Good | ● Good | ● Good | ● Not enough |
| Amy | Station 3 | ● Good | ● Bad | ● Good | ● Not enough |
| Tom | Station 5 | ● Good | ● Good | ● Good | ● Not enough |
| Charlie | Station 1 | ● Good | ● Average | ● Good | ● Good |
| Alison | Station 8 | ● Good | ● Good | ● Bad | ● Good |
| Erin | Station 2 | ● Good | ● Good | ● Good | ● Good |
| John | Station 10 | ● Good | ● Good | ● Average | ● Average |
| Ron | Station 9 | ● Good | ● Good | ● Good | ● Good |

● Good fit   ● Average fit   ● Bad fit   ● Not enough data

FIG. 16

WORKER PROFILE & DRISHTI CERTIFICATES

Max

Age: 44
Sex: M
Height: 5'10
Weight: 180 lbs

Hand reach: 2'0
Hand length: 7.45 in
Eye sight: 20/20

Notes:

| | Experience | Accuracy | Speed vs Standard | Ergonomics Fit % | | Drishti Certified |
|---|---|---|---|---|---|---|
| Line 1 ST 1 | 202 hrs | 95% | 125% | 95% | | Yes |
| Line 1 ST 2 | 21 hrs | 99% | 95% | 45% | | No |
| Line 2 ST 1 | 94 hrs | 81% | 106% | 100% | | Yes |
| Line 2 ST 2 | 0 hrs | NA | NA | 95% | | No |
| ... | | | | | | |

SYSTEMS AND METHODS FOR AUTOMATIC JOB ASSIGNMENT

CROSS-REFERENCE TO RELATED APPLICATION

This application claims the benefit of U.S. Provisional Patent Application No. 62/581,541 filed Nov. 3, 2017, entitled "System and Method for Automated Process Identification and Validation," by Prasad Akella et al., which is hereby incorporated by reference.

FIELD OF THE INVENTION

The present invention relates to the field of production systems. More specifically, the present invention relates to methods and systems for providing increased efficiency in production systems employing workers in varying settings from factories to pharmacies to nursing homes and retail stores.

BACKGROUND

Workers inherently perform the same physical tasks, e.g., tasks related to producing goods and services, in different ways. Some of the differences relate to the differences workers have in their abilities, physical, cognitive, learning and training to name a few. For instance, some are more dexterous than others while others might show diurnal variation in their abilities. While others might handle different assembly tasks differently. Even the same worker may perform the same task differently over time, depending on their current physical abilities. These variations, regardless of their causes, imply that it is important to continually match workers to the different tasks that need to be executed on a production line in order to achieve the highest process efficiency while maximally protecting the worker's health and utilizing their skills.

Manufacturers currently build worker schedules manually, often using institutional or anecdotal knowledge and manual observation of worker capacities. These schedules, whether built manually or using tools like Excel, are based on fundamentally deterministic models that are not statistical in nature. Many of these schedule building tools also do not take into account real-time changes in worker's abilities, etc.

It would be advantageous to provide a system and methodology that take into consideration additional information, even statistical information, concerning workers, their abilities, and the tasks they perform on a production line, for instance.

SUMMARY

Embodiments of the present invention provide a deep and continuous data set including process data, quality data, specific actor data, and ergonomic data (among others) to automatically determine job assignments that maximize efficiency, quality and actor safety. Using the data set, tasks may be assigned to actors based on objective statistical data such as skills, task requirements, ergonomics and time availability. Assigning tasks in this way can provide unique value for manufacturers who currently conduct similar analyses using only minimal observational data.

In various embodiments, a computer implemented method of automatically determining a work task assignment for an actor based on captured actions of the actor is disclosed. The method includes receiving a sensor stream at a computing device, the sensor stream including sensor information obtained from a sensor operable to sense progress of a work task, using the computing device executing an engine, and identifying a plurality of actions recorded within the sensor stream that are performed by the actor. The computing device is used to store the received sensor stream and identities of the plurality of actions recorded therein in a memory resident data structure of the computing device, and a respective identities of each of the plurality of actions are mapped to the sensor stream. The computing device and the engine application are used to characterize the respective actions performed by each of the plurality of actors to produce determined characterizations thereof. Based on the determined characterizations of the actor performing the plurality of actions, and the cost function that the business wishes to optimize, the work task assignment is automatically determined by the proposed system for the actor.

In various embodiments, a computer implemented method of determining a work task assignment for an actor within a production system is disclosed. The method includes receiving a sensor stream at a computing device, the sensor stream including sensor information obtained from a sensor operable to sense progress of a work task performed by a plurality of actors, receiving with the computing device an identity of each of a plurality of actors identified within the sensor stream, using the computing device and an engine to identify an action within the sensor stream that is performed by each of the plurality of actors performing the work task, using the computing device to store, in a data structure, the received sensor stream, an identity of each action, and an identity of each of the plurality of actors, using the computing device to map respective actions performed by each of the plurality of actors to the sensor stream, using the computing device and the engine to characterize the respective actions performed by each of the plurality of actors to produce determined characterizations thereof, and based on the determined characterizations of the plurality of actors performing the action, automatically determining the work task assignment which assigns an actor of the plurality of actors to perform the action.

In various embodiments, a system is disclosed, the system including a processor coupled to a bus, a sensor, in communication with the bus, and operable to sense progress of a work task, and a memory coupled to the bus and including instructions that when executed cause the system to implement a method of automatically determining, in real-time, a work task assignment for an actor. The method includes receiving a sensor stream including sensor information obtained from the sensor and executing an engine to identify a plurality of actions within the sensor stream that are performed by an actor The method further includes storing, in a memory resident data structure of the memory, the received sensor stream and identities of the plurality of actions, where respective identities of each of the plurality of actions are mapped to the sensor stream, and using the engine to characterize each of the identified plurality of actions performed by the actor and to produce determined characterizations thereof. Based on the determined characterizations of the actor performing the plurality of actions, the work task assignment for the actor is automatically determined.

In various embodiments, the determined characterizations comprise ergonomics of the actor used to perform each of the identified plurality of actions.

In various embodiments, the determined characterizations comprise a skill level of the actor used to perform each of the identified plurality of actions.

In various embodiments, the determined characterizations comprise a time required for the actor to perform each of the identified plurality of actions.

In various embodiments, the method further includes determining a certification expertise indicating that the actor is certified to a standard based on the determined characterizations of the actor performing the plurality of actions.

In various embodiments, the sensor stream includes video frames.

In various embodiments, the sensor stream includes thermal sensor data.

In various embodiments, the sensor stream includes force sensor data.

In various embodiments, the sensor stream includes audio sensor data.

In various embodiments, the sensor stream includes one of: video frames, thermal sensor data, force sensor data, audio sensor data, and light sensor data.

While various embodiments in accordance with the present disclosure have been specifically described within this Summary, it is noted that the claimed subject matter are not limited in any way by these various embodiments.

BRIEF DESCRIPTION OF THE DRAWINGS

Within the accompanying drawings, various embodiments in accordance with the present disclosure are illustrated by way of example and not by way of limitation. It is noted that like reference numerals denote similar elements throughout the drawings.

FIG. 16 shows an exemplary job assignment output according to embodiments of the present invention.

DETAILED DESCRIPTION

As used herein the term process can include processes, procedures, transactions, routines, practices, and the like. As used herein the term sequence can include sequences, orders, arrangements, and the like. As used herein the term action can include actions, steps, tasks, activity, motion, movement, and the like. As used herein the term object can include objects, parts, components, items, elements, pieces, assemblies, sub-assemblies, and the like. As used herein a process can include a set of actions or one or more subsets of actions, arranged in one or more sequences, and performed on one or more objects by one or more actors. As used herein a cycle can include a set of processes or one or more subsets of processes performed in one or more sequences. As used herein a sensor stream can include a video sensor stream, thermal sensor stream, infrared sensor stream, hyperspectral sensor stream, audio sensor stream, depth data stream, and the like. As used herein frame based sensor stream can include any sensor stream that can be represented by a two or more dimensional array of data values. As used herein the term parameter can include parameters, attributes, or the like. As used herein the term indicator can include indicators, identifiers, labels, tags, states, attributes, values or the like. As used herein the term feedback can include feedback, commands, directions, alerts, alarms, instructions, orders, and the like. As used herein the term actor can include actors, workers, employees, operators, assemblers, contractors, associates, managers, users, entities, humans, cobots, robots, and the like as well as combinations of them. As used herein the term robot can include a machine, device, apparatus or the like, especially one programmable by a computer, capable of carrying out a series of actions automatically. The actions can be autonomous, semi-autonomous, assisted, or the like. As used herein the term cobot can include a robot intended to interact with humans in a shared workspace. As used herein the term package can include packages, packets, bundles, boxes, containers, cases, cartons, kits, and the like. As used herein, real time can include responses within a given latency, which can vary from sub-second to seconds.

Figure 1:
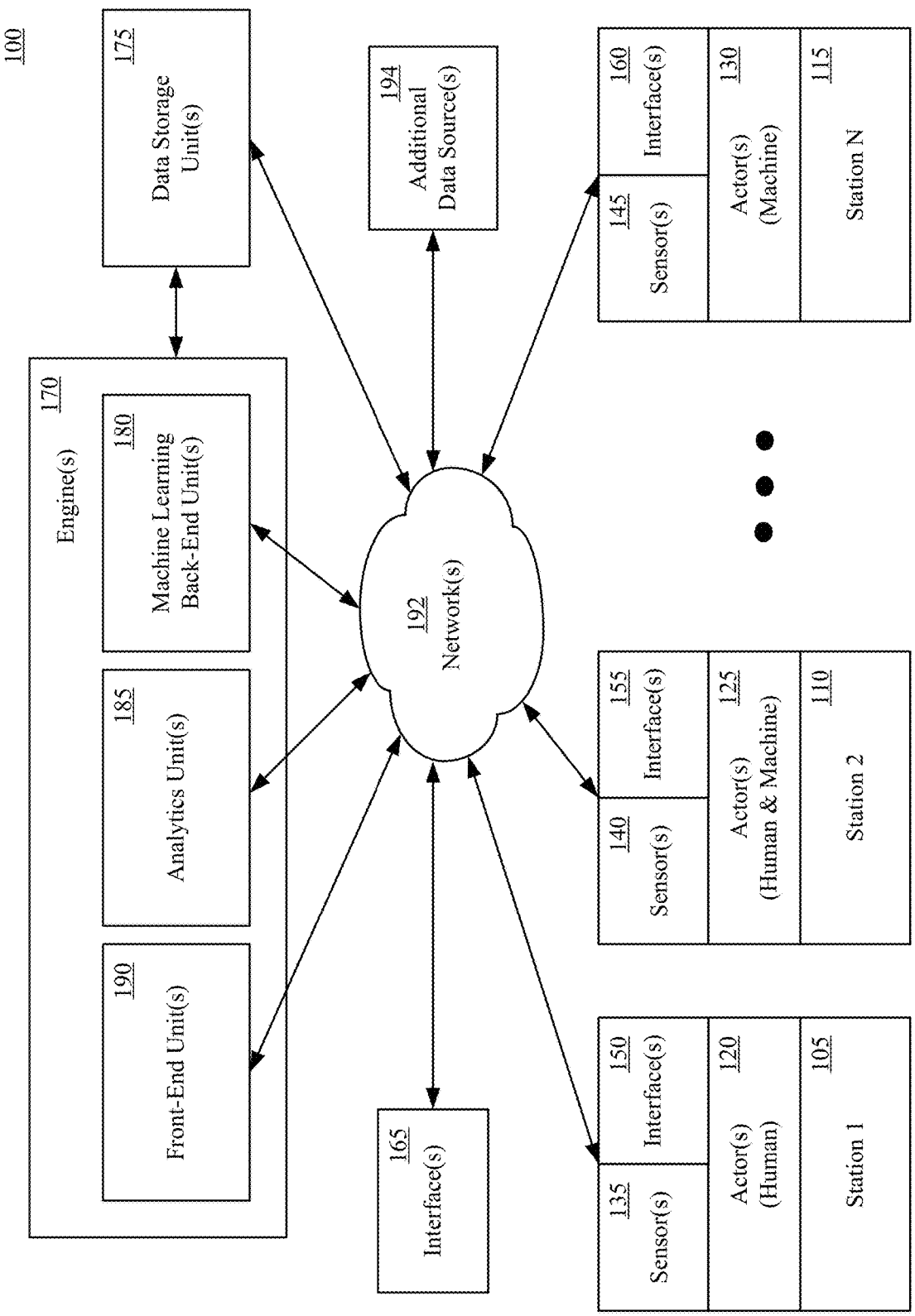
FIG. 1 shows an action recognition and analytics system, in accordance with aspect of the present technology.

Referring to FIG. 1 an action recognition and analytics system, in accordance with aspect of the present technology, is shown. The action recognition and analytics system 100 can be deployed in a manufacturing, health care, warehousing, shipping, retail, restaurant or similar context. A manufacturing context, for example, can include one or more stations 105-115 and one or more actors 120-130 disposed at the one or more stations. The actors can include humans, machine or any combination therefore. For example, individual or multiple workers can be deployed at one or more stations along a manufacturing assembly line. One or more robots can be deployed at other stations. A combination of one or more workers and/or one or more robots can be deployed additional stations It is to be noted that the one or more stations 105-115 and the one or more actors are not generally considered to be included in the system 100.

In a health care implementation, an operating room can comprise a single station implementation. A plurality of sensors, such as video cameras, thermal imaging sensors, depth sensors, or the like, can be disposed non-intrusively at various positions around the operating room. One or more additional sensors, such as audio, temperature, acceleration, torque, compression, tension, or the like sensors, can also be disposed non-intrusively at various positions around the operating room.

In a shipping implementation, the plurality of stations may represent different loading docks, conveyor belts, forklifts, sorting stations, holding areas, and the like. A plurality of sensors, such as video cameras, thermal imaging sensors, depth sensors, or the like, can be disposed non-intrusively at various positions around the loading docks, conveyor belts, forklifts, sorting stations, holding areas, and the like. One or more additional sensors, such as audio, temperature, acceleration, torque, compression, tension, or the like sensors, can also be disposed non-intrusively at various positions.

In a retailing implementation, the plurality of stations may represent one or more loading docks, one or more stock rooms, the store shelves, the point of sale (e.g. cashier stands, self-checkout stands and auto-payment geofence), and the like. A plurality of sensors such as video cameras, thermal imaging sensors, depth sensors, or the like, can be disposed non-intrusively at various positions around the loading docks, stock rooms, store shelves, point of sale stands and the like. One or more additional sensors, such as audio, acceleration, torque, compression, tension, or the like sensors, can also be disposed non-intrusively at various positions around the loading docks, stock rooms, store shelves, point of sale stands and the like.

In a warehousing or online retailing implementation, the plurality of stations may represent receiving areas, inventory storage, picking totes, conveyors, packing areas, shipping areas, and the like. A plurality of sensors, such as video cameras, thermal imaging sensors, depth sensors, or the like, can be disposed non-intrusively at various positions around the receiving areas, inventory storage, picking totes, conveyors, packing areas, and shipping areas. One or more additional sensors, such as audio, temperature, acceleration, torque, compression, tension, or the like sensors, can also be disposed non-intrusively at various positions.

Aspect of the present technology will be herein further described with reference to a manufacturing context so as to best explain the principles of the present technology without obscuring aspects of the present technology. However, the present technology as further described below can also be readily applied in health care, warehousing, shipping, retail, restaurants, and numerous other similar contexts.

The action recognition and analytics system 100 can include one or more interfaces 135-165. The one or more interface 135-165 can include one or more sensors 135-145 disposed at the one or more stations 105-115 and configured to capture streams of data concerning cycles, processes, actions, sequences, object, parameters and or the like by the one or more actors 120-130 and or at the station 105-115. The one or more sensors 135-145 can be disposed non-intrusively, so that minimal to changes to the layout of the assembly line or the plant are required, at various positions around one or more of the stations 105-115. The same set of one or more sensors 135-145 can be disposed at each station 105-115, or different sets of one or more sensors 135-145 can be disposed at different stations 105-115. The sensors 135-145 can include one or more sensors such as video cameras, thermal imaging sensors, depth sensors, or the like. The one or more sensors 135-145 can also include one or more other sensors, such as audio, temperature, acceleration, torque, compression, tension, or the like sensors.

The one or more interfaces 135-165 can also include but not limited to one or more displays, touch screens, touch pads, keyboards, pointing devices, button, switches, control panels, actuators, indicator lights, speakers, Augmented Reality (AR) interfaces, Virtual Reality (VR) interfaces, desktop Personal Computers (PCs), laptop PCs, tablet PCs, smart phones, robot interfaces, cobot interfaces. The one or more interfaces 135-165 can be configured to receive inputs from one or more actors 120-130, one or more engines 170 or other entities. Similarly, the one or more interfaces 135-165 can be configured to output to one or more actors 120-130, one or more engine 170 or other entities. For example, the one or more front-end units 190 can output one or more graphical user interfaces to present training content, work charts, real time alerts, feedback and or the like on one or more interfaces 165, such displays at one or more stations 120-130, at management portals on tablet PCs, administrator portals as desktop PCs or the like. In another example, the one or more front-end units 190 can control an actuator to push a defective unit of the assembly line when a defect is detected. The one or more front-end units can also receive responses on a touch screen display device, keyboard, one or more buttons, microphone or the like from one or more actors. Accordingly, the interfaces 135-165 can implement an analysis interface, mentoring interface and or the like of the one or more front-end units 190.

The action recognition and analytics system 100 can also include one or more engines 170 and one or more data storage units 175. The one or more interfaces 135-165, the one or more data storage units 175, the one or more machine learning back-end units 180, the one or more analytics units 185, and the one or more front-end units 190 can be coupled together by one or more networks 192. It is also to be noted that although the above described elements are described as separate elements, one or more elements of the action recognition and analytics system 100 can be combined together or further broken into different elements.

The one or more engines 170 can include one or more machine learning back-end units 180, one or more analytics units 185, and one or more front-end units 190. The one or more data storage units 175, the one or more machine learning back-end units 180, the one or more analytics units 185, and the one or more analytics front-end units 190 can be implemented on a single computing device, a common set of computing devices, separate computing device, or different sets of computing devices that can be distributed across the globe inside and outside an enterprise. Aspects of the one or more machine learning back-end units 180, the one or more analytics units 185 and the one or more front-end units 190, and or other computing units of the action recognition and analytics system 100 can be implemented by one or more central processing units (CPU), one or more graphics processing units (GPU), one or more tensor processing units (TPU), one or more digital signal processors (DSP), one or more microcontrollers, one or more field programmable gate arrays and or the like, and any combination thereof. In addition, the one or more data storage units 175, the one or more machine learning back-end units 180, the one or more analytics units 185, and the one or more front-end units 190 can be implemented locally to the one or more stations 105-115, remotely from the one or more stations 105-115, or any combination of locally and remotely. In one example, the one or more data storage units 175, the one or more machine learning back-end units 180, the one or more analytics units 185, and the one or more front-end units 190 can be implemented on a server local (e.g., on site at the manufacturer) to the one or more stations 105-115. In another example, the one or more machine learning back-end units 135, the one or more storage units 140 and analytics front-end units 145 can be implemented on a cloud computing service remote from the one or more stations 105-115. In yet another example, the one or more data storage units 175 and the one or more machine learning back-end units 180 can be implemented remotely on a server of a vendor, and one or more data storage units 175 and the one or more front-end units 190 are implemented locally on a server or computer of the manufacturer. In other examples, the one or more sensors 135-145, the one or more machine learning back-end units 180, the one or more front-end unit 190, and other computing units of the action recognition and analytics system 100 can perform processing at the edge of the network 192 in an edge computing implementation. The above example of the deployment of one or more computing devices to implement the one or more interfaces 135-165, the one or more engines 170, the one or more data storage units 140 and one or more analytics front-end units 145, are just some of the many different configuration for implementing the one or more machine learning back-end units 135, one or more data storage units 140. Any number of computing devices, deployed locally, remotely, at the edge or the like can be utilized for implementing the one or more machine learning back-end units 135, the one or more data storage units 140, the one or more analytics front-end units 145 or other computing units.

The action recognition and analytics system 100 can also optionally include one or more data compression units associated with one or more of the interfaces 135-165. The data compression units can be configured to compress or decompress data transmitted between the one or more interface 135-165, and the one or more engines 170. Data compression, for example, can advantageously allow the sensor data from the one or more interface 135-165 to be transmitted across one or more existing networks 192 of a manufacturer. The data compression units can also be integral to one or more interfaces 135-165 or implemented separately. For example, video capture sensors may include an integral Motion Picture Expert Group (MPEG) compression unit (e.g., H-264 encoder/decoder). In an exemplary implementation, the one or more data compression units can use differential coding and arithmetic encoding to obtain a 20× reduction in the size of depth data from depth sensors. The data from a video capture sensor can comprise roughly 30 GB of H.264 compressed data per camera, per day for a factory operation with three eight-hour shifts. The depth data can comprise roughly another 400 GB of uncompressed data per sensor, per day. The depth data can be compressed by an algorithm to approximately 20 GB per sensor, per day. Together, a set of a video sensor and a depth sensor can generate approximately 50 GB of compressed data per day. The compression can allow the action recognition and analytics system 100 to use a factory's network 192 to move and store data locally or remotely (e.g., cloud storage).

The action recognition and analytics system 100 can also be communicatively coupled to additional data sources 194, such as but not limited to a Manufacturing Execution Systems (MES), warehouse management system, or patient management system. The action recognition and analytics system 100 can receive additional data, including one or more additional sensor streams, from the additional data sources 194. The action recognition and analytics system 100 can also output data, sensor streams, analytics result and or the like to the additional data sources 194. For example, the action recognition can identify a barcode on an object and provide the barcode input to a MES for tracking.

The action recognition and analytics system 100 can continually measure aspects of the real-world, making it possible to describe a context utilizing vastly more detailed data sets, and to solve important business problems like line balancing, ergonomics, and or the like. The data can also reflect variations over time. The one or more machine learning back-end units 170 can be configured to recognize, in real time, one or more cycles, processes, actions, sequences, objects, parameters and the like in the sensor streams received from the plurality of sensors 135-145. The one or more machine learning back-end units 180 can recognize cycles, processes, actions, sequences, objects, parameters and the like in sensor streams utilizing deep learning, decision tree learning, inductive logic programming, clustering, reinforcement learning, Bayesian networks, and or the like.

Figure 2:
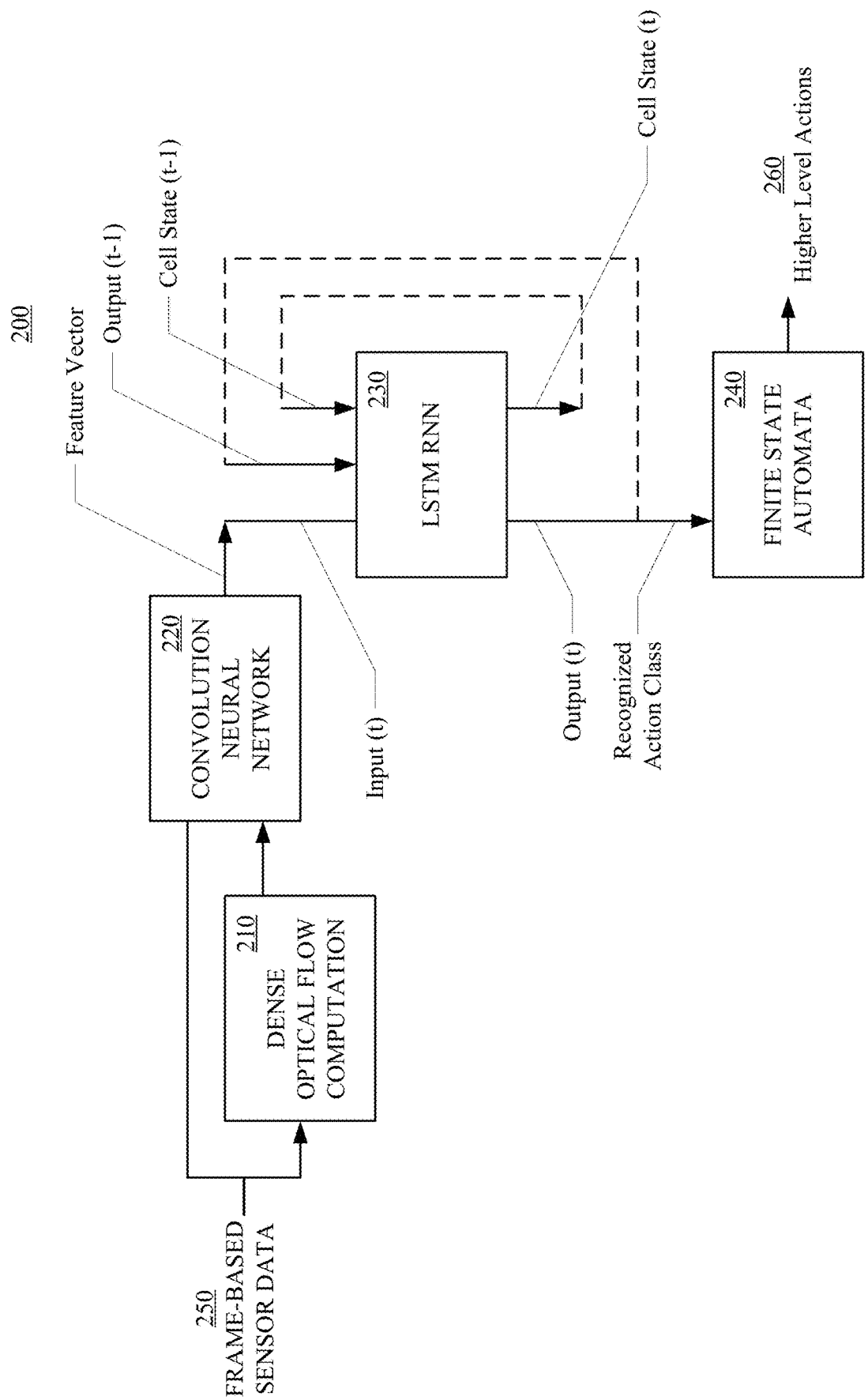
FIG. 2 shows an exemplary deep learning type machine learning back-end unit, in accordance with aspects of the present technology.

Referring now to FIG. 2, an exemplary deep learning type machine learning back-end unit, in accordance with aspects of the present technology, is shown. The deep learning unit 200 can be configured to recognize, in real time, one or more cycles, processes, actions, sequences, objects, parameters and the like in the sensor streams received from the plurality of sensors 120-130. The deep learning unit 200 can include a dense optical flow computation unit 210, a Convolution Neural Networks (CNNs) 220, a Long Short Term Memory (LSTM) Recurrent Neural Network (RNN) 230, and a Finite State Automata (FSA) 240. The CNNs 220 can be based on two-dimensional (2D) or three-dimensional (3D) convolutions. The dense optical flow computation unit 210 can be configured to receive a stream of frame-based sensor data 250 from sensors 120-130. The dense optical flow computation unit 210 can be configured to estimate an optical flow, which is a two-dimension (2D) vector field where each vector is a displacement vector showing the movement of points from a first frame to a second frame. The CNNs 220 can receive the stream of frame-based sensor data 250 and the optical flow estimated by the dense optical flow computation unit 210. The CNNs 220 can be applied to video frames to create a digest of the frames. The digest of the frames can also be referred to as the embedding vector. The digest retains those aspects of the frame that help in identifying actions, such as the core visual clues that are common to instances of the action in question.

In a three-dimensional Convolution Neural Network (3D CNN) based approach, spatio-temporal convolutions can be performed to digest multiple video frames together to recognize actions. For 3D CNN, the first two dimension can be along space, and in particular the width and height of each video frame. The third dimension can be along time. The neural network can learn to recognize actions not just from the spatial pattern in individual frame, but also jointly in space and time. The neural network is not just using color patterns in one frame to recognize actions. Instead, the neural network is using how the pattern shifts with time (i.e., motion cues) to come up with its classification. According the 3D CNN is attention driven, in that it proceeds by identifying 3D spatio-temporal bounding boxes as Regions of Interest (RoI) and focuses on them to classify actions.

In one implementation, the input to the deep learning unit 200 can include multiple data streams. In one instance, a video sensor signal, which includes red, green and blue data streams, can comprise three channels. Depth image data can comprise another channel. Additional channels can accrue from temperature, sound, vibration, data from sensors (e.g., torque from a screwdriver) and the like. From the RGB and depth streams, dense optical flow fields can be computed by the dense optical flow computation unit 210 and fed to the Convolution Neural Networks (CNNs) 220. The RGB and depth streams can also be fed to the CNNs 220 as additional streams of derived data.

The Long Short Term Memory (LSTM) Recurrent Neural Network (RNN) 230 can be fed the digests from the output of the Convolution Neural Networks (CNNs) 220. The LSTM can essentially be a sequence identifier that is trained to recognize temporal sequences of sub-events that constitute an action. The combination of the CNNs and LSTM can be jointly trained, with full back-propagation, to recognize low-level actions. The low-level actions can be referred to as atomic actions, like picking a screw, picking a screwdriver, attaching screw to screwdriver and the like. The Finite State Automata (FSA) 240 can be mathematical models of computations that include a set of state and a set of rules that govern the transition between the states based on the provided input. The FSA 240 can be configured to recognize higher-level actions 260 from the atomic actions. The high-level actions 260 can be referred to as molecular actions, for example turning a screw to affix a hard drive to a computer chassis. The CNNs and LSTM can be configured to perform supervised training on the data from the multiple sensor streams. In one implementation, approximately 12 hours of data, collected over the course of several days, can be utilized to train the CNNs and LSTM combination.

Figure 3:
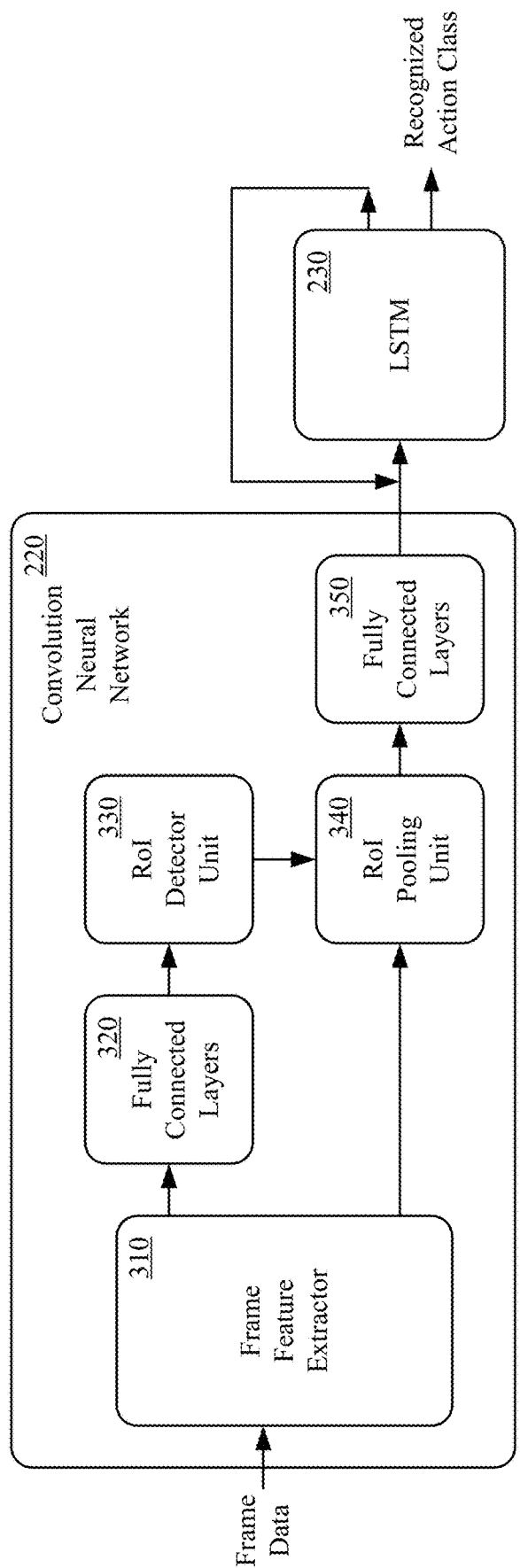
FIG. 3 shows an exemplary Convolution Neural Networks (CNNs) and Long Short Term Memory (LSTM) Recurrent Neural Network (RNN), in accordance with aspects of the present technology.
Figure 4:
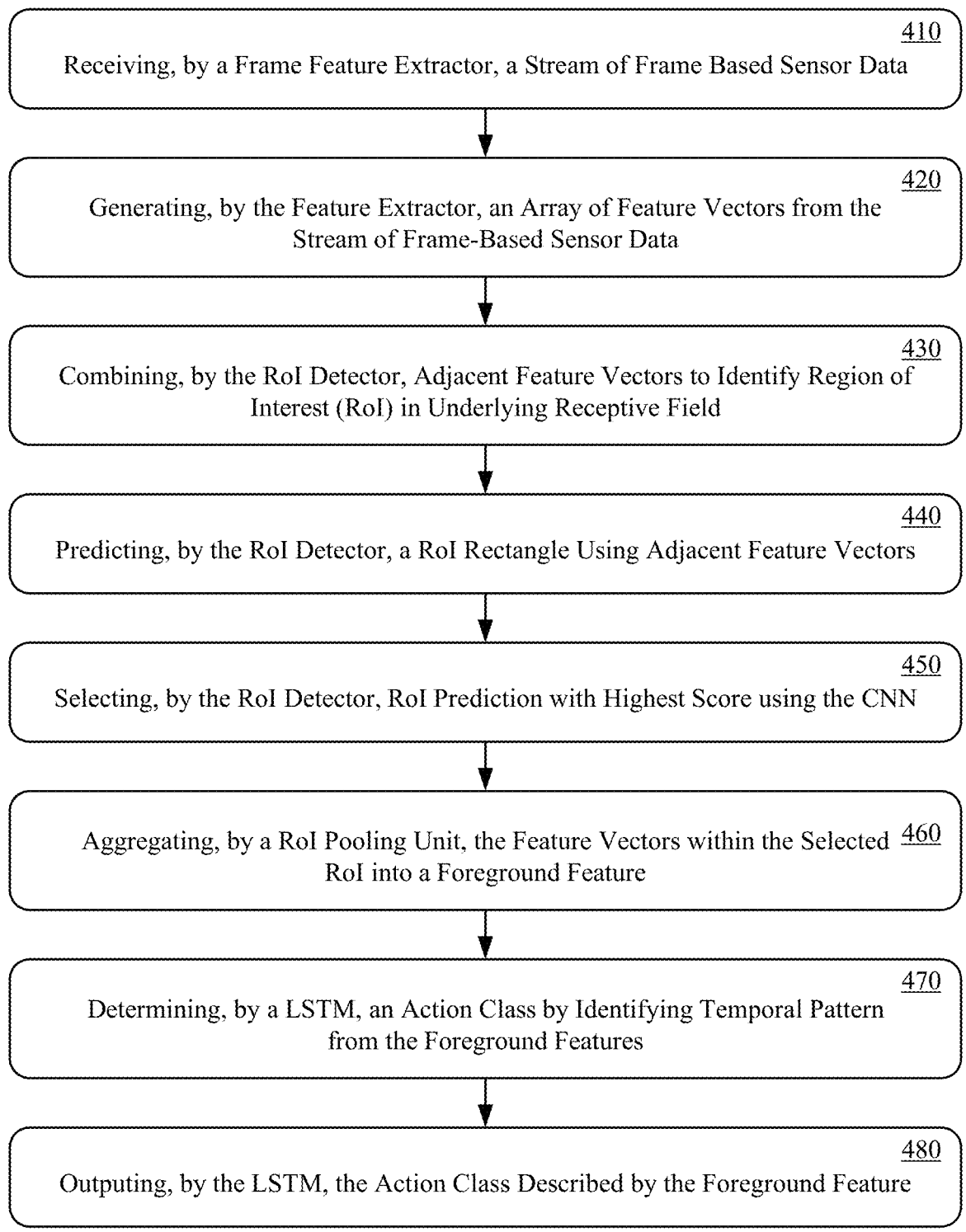
FIG. 4 shows an exemplary method of detecting actions in a sensor stream, in accordance with aspects of the present technology.

Referring now to FIG. 3, an exemplary Convolution Neural Networks (CNNs) and Long Short Term Memory (LSTM) Recurrent Neural Network (RNN), in accordance with aspects of the present technology, is shown. The CNNs can include a frame feature extractor 310, a first Fully Connected (FC) layer 320, a Region of Interest (RoI) detector unit 330, a RoI pooling unit 340, and a second Fully Connected (FC) layer 350. The operation of the CNNs and LSTM will be further explained with reference to FIG. 4, which shows an exemplary method of detecting actions in a sensor stream.

The frame feature extractor 310 of the Convolution Neural Networks (CNNs) 220 can receive a stream of frame-based sensor data, at 410. At 420, the frame feature extractor 310 can perform a two-dimensional convolution operation on the received video frame and generate a two-dimensional array of feature vectors. The frame feature extractor 310 can work on the full resolution image, wherein a deep network is effectively sliding across the image generating a feature vector at each stride position. Thus, each element of the 2D feature vector array is a descriptor for the corresponding receptive field (e.g., fixed portion of the underlying image). The first Fully Connected (FC) layer can flatten the high-level features extracted by the frame feature extractor 310, and provide additional non-linearity and expressive power, enabling the machine to learn complex non-linear combinations of these features.

At 430, the RoI detector unit 330 can combine neighboring feature vectors to make a decision on whether the underlying receptive field belongs to a Region of Interest (RoI) or not. If the underlying receptive field belongs to a RoI, a RoI rectangle can be predicted from the same set of neighboring feature vectors, at 440. At, 450, a RoI rectangle with a highest score can be chosen by the RoI detector unit 330. For the chosen RoI rectangle, the feature vectors lying within it can be aggregated by the RoI pooling unit 340, at 460. The aggregated feature vector is a digest/descriptor for the foreground for that video frame.

In one implementation, the RoI detector unit 330 can determine a static RoI. The static RoI identifies a Region of Interest (RoI) within an aggregate set of feature vectors describing a video frame, and generates a RoI area for the identified RoI. A RoI area within a video frame can be indicated with a RoI rectangle that encompasses an area of the video frame designated for action recognition, such as an area in which actions are performed in a process. Alternatively, the RoI area can be designated with a box, circle, highlighted screen, or any other geometric shape or indicator having various scales and aspect ratios used to encompass a RoI. The area within the RoI rectangle is the area within the video frame to be processed by the Long Short Term Memory (LSTM) for action recognition.

The Long Short Term Memory (LSTM) can be trained using a RoI rectangle that provides, both, adequate spatial context within the video frame to recognize actions and independence from irrelevant portions of the video frame in the background. The trade-off between spatial context and background independence ensures that the static RoI detector can provide clues for the action recognition while avoiding spurious unreliable signals within a given video frame.

In another implementation, the RoI detector unit 330 can determine a dynamic RoI. A RoI rectangle can encompass areas within a video frame in which an action is occurring. By focusing on areas in which action occurs, the dynamic RoI detector enables recognition of actions outside of a static RoI rectangle while relying on a smaller spatial context, or local context, than that used to recognize actions in a static RoI rectangle.

In one implementation, the RoI pooling unit 340 extracts a fixed-sized feature vector from the area within an identified RoI rectangle, and discards the remaining feature vectors of the input video frame. The fixed-sized feature vector, or foreground feature, includes the feature vectors generated by the video frame feature extractor that are located within the coordinates indicating a RoI rectangle as determined by the RoI detector unit 330. Because the RoI pooling unit 340 discards feature vectors not included within the RoI rectangle, the Convolution Neural Networks (CNNs) 220 analyzes actions within the RoI only, thus ensuring that unexpected changes in the background of a video frame are not erroneously analyzed for action recognition.

In one implementation, the Convolution Neural Networks (CNNs) 220 can be an Inception ResNet. The Inception ResNet can utilize a sliding window style operation. Successive convolution layers output a feature vector at each point of a two-dimensional grid. The feature vector at location (x,y) at level l can be derived by weighted averaging features from a small local neighborhood (aka receptive field) N around the (x,y) at level l−1 followed by a pointwise non-linear operator. The non-linear operator can be the RELU (max(0,x)) operator.

In the sliding window, there can be many more than 7×7 points at the output of the last convolution layer. A Fully Connected (FC) convolution can be taken over the feature vectors from the 7×7 neighborhoods, which is nothing but applying one more convolution. The corresponding output represents the Convolution Neural Networks (CNNs) output at the matching 224×224 receptive field on the input image. This is fundamentally equivalent to applying the CNNs to each sliding window stop. However, no computation is repeated, thus keeping the inferencing computation cost real time on Graphics Processing Unit (GPU) based machines.

The convolution layers can be shared between RoI detector 330 and the video frame feature extractor 310. The RoI detector unit 330 can identify the class independent rectangular region of interest from the video frame. The video frame feature extractor can digest the video frame into feature vectors. The sharing of the convolution layers improves efficiency, wherein these expensive layers can be run once per frame and the results saved and reused.

One of the outputs of the Convolution Neural Networks (CNNs) is the static rectangular Region of Interest (RoI). The term "static" as used herein denotes that the RoI does not vary greatly from frame to frame, except when a scene change occurs, and it is also independent of the output class.

A set of concentric anchor boxes can be employed at each sliding window stop. In one implementation, there can be nine anchor boxes per sliding window stop for combinations of 3 scales and 3 aspect ratios. Therefore, at each sliding window stop there are two set of outputs. The first set of outputs can be a Region of Interest (RoI) present/absent that includes 18 outputs of the form 0 or 1. An output of 0 indicates the absence of a RoI within the anchor box, and an output of 1 indicates the presence of a RoI within the anchor box. The second set of outputs can include Bounding Box (BBox) coordinates including 36 floating point outputs indicating the actual BBox for each of the 9 anchor boxes. The BBox coordinates are to be ignored if the RoI present/absent output indicates the absence of a RoI.

For training, sets of video frames with a per-frame Region of Interest (RoI) rectangle are presented to the network. In frames without a RoI rectangle, a dummy 0×0 rectangle can be presented. The Ground Truth for individual anchor boxes can be created via the Intersection over Union (IoU) of rectangles. For the $i_{th}$ anchor box $\vec{b}_i=\{x_i, y_i, w_i, h_i\}$ the derived Ground Truth for the RoI presence probability can be determined by Equation 1:

$$p_i^* = \begin{cases} 1 & IoU(\vec{b}_i, \vec{g}) >= 0.7 \\ 0 & IoU(\vec{b}_i, \vec{g}) <= 0.1 \\ \text{box unused for training} \end{cases}$$

where $\vec{g}=\{x_g, y_g, w_g, h_g\}$ is the Ground Truth RoI box for the entire frame.

The loss function can be determined by Equation 2:

$$L(p_i, p_i^*, \vec{b}_i, \vec{g}) = \sum_i [-p_i^* \log[p_i(S(x_i - x_g) + S(y_i] - y_g]) + S(w_i - w_g) + S(h_i - h_g))$$

where $p_i$ is the predicted probability for presence of Region of Interest (RoI) in the $i_{th}$ anchor box and the smooth loss function can be defined by Equation 3:

$$S(x) = \begin{cases} 0.5x^2 & |x| < 1 \\ |x| - 0.5 & \text{otherwise} \end{cases}$$

The left term in the loss function is the error in predicting the probability of the presence of a RoI, while the second term is the mismatch in the predicted Bounding Box (BBox). It should be noted that the second term vanishes when the ground truth indicates that there is no RoI in the anchor box.

The static Region of Interest (RoI) is independent of the action class. In another implementation, a dynamic Region of Interest (RoI), that is class dependent, is proposed by the CNNs. This takes the form of a rectangle enclosing the part of the image where the specific action is occurring. This increases the focus of the network and takes it a step closer to a local context-based action recognition.

Once a Region of Interest (RoI) has been identified, the frame feature can be extracted from within the RoI. These will yield a background independent frame digest. But this feature vector also needs to be a fixed size so that it can be fed into the Long Short Term Memory (LSTM). The fixed size can be achieved via RoI pooling. For RoI pooling, the RoI can be tiled up into 7×7 boxes. The mean of all feature vectors within a tile can then be determined. Thus, 49 feature vectors that are concatenated from the frame digest can be produced. The second Fully Connected (FC) layer 350 can provide additional non-linearity and expressive power to the machine, creating a fixed size frame digest that can be consumed by the LSTM 230.

At 470, successive foreground features can be fed into the Long Short Term Memory (LSTM) 230 to learn the temporal pattern. The LSTM 230 can be configured to recognize patterns in an input sequence. In video action recognition, there could be patterns within sequences of frames belonging to a single action, referred to as intra action patterns. There could also be patterns within sequences of actions, referred to as inter action patterns. The LSTM can be configured to learn both of these patterns, jointly referred to as temporal patterns. The Long Short Term Memory (LSTM) analyzes a series of foreground features to recognize actions belonging to an overall sequence. In one implementation, the LSTM outputs an action class describing a recognized action associated with an overall process for each input it receives, at 480. In another implementation, each class action is comprised of sets of actions describing actions associated with completing an overall process. Each action within the set of actions can be assigned a score indicating a likelihood that the action matches the action captured in the input video frame. Each action may be assigned a score such that the action with the highest score is designated the recognized action class.

Foreground features from successive frames can be feed into the Long Short Term Memory (LSTM). The foreground feature refers to the aggregated feature vectors from within the Region of Interest (RoI) rectangles. The output of the LSTM at each time step is the recognized action class. The loss for each individual frame is the cross entropy softmax loss over the set of possible action classes. A batch is defined as a set of three randomly selected set of twelve frame sequences in the video stream. The loss for a batch is defined as the frame loss averaged over the frame in the batch. The numbers twelve and three are chose empirically. The overall LSTM loss function is given by Equation 4:

$$L(B, \{S_1, S_2, \ldots, S_{\|B\|}\}) = \sum_{k=1}^{\|B\|} \sum_{t=1}^{\|S_k\|} \sum_{i=1}^{\|A\|} \Box - \left(\frac{e^{a_{t_i}}}{\sum_{j=1}^{\|A\|} e^{a_{t_j}}}\right) \log a_{t_i}^*$$

where B denotes a batch of $\|B\|$ frame sequences $\{S_1, S_2, \ldots, S_{\|B\|}\}$. $S_k$ comprises a sequence of $\|S_k\|$ frames, wherein in the present implementation $\|B\|=3$ and $\|S_k\|=12$ k. A denotes the set of all action classes, $a_{t_i}$ denotes the $i_{th}$ action class score for the $t_{th}$ frame from LSTM and $a_{t_i}^*$ denotes the corresponding Ground Truth.

Referring again to FIG. 1, the machine learning back-end unit 135 can utilize custom labelling tools with interfaces optimized for labeling RoI, cycles and action. The labelling tools can include both standalone application built on top of Open source Computer Vision (OpenCV) and web browser application that allow for the labeling of video segment.

Figure 5:
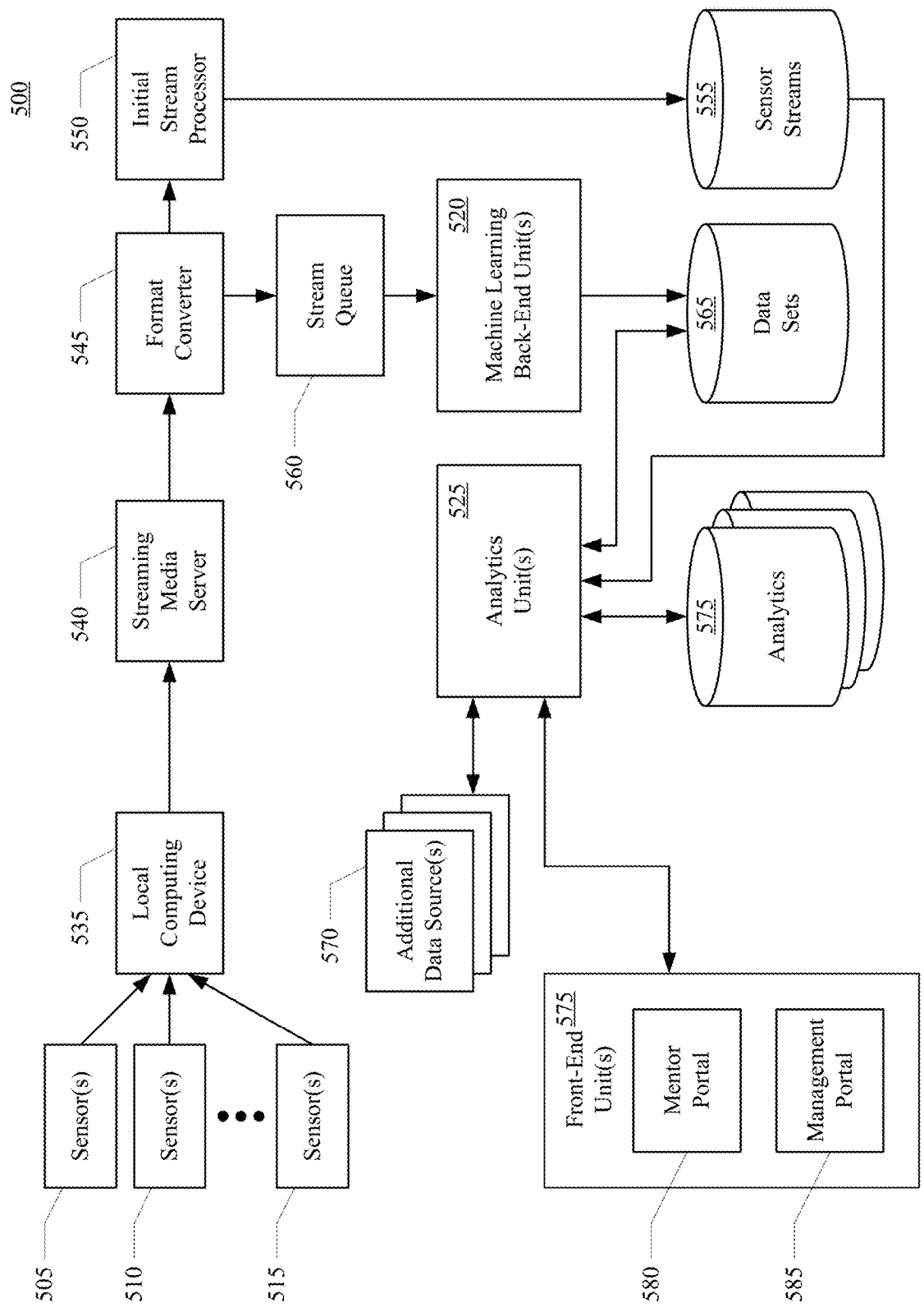
FIG. 5 shows an action recognition and analytics system, in accordance with aspect of the present technology.

Referring now to FIG. 5, an action recognition and analytics system, in accordance with aspect of the present technology, is shown. Again, the action recognition and analytics system 500 can be deployed in a manufacturing, health care, warehousing, shipping, retail, restaurant, or similar context. The system 500 similarly includes one or more sensors 505-515 disposed at one or more stations, one or more machine learning back-end units 520, one or more analytics units 525, and one or more front-end units 530. The one or more sensors 505-515 can be coupled to one or more local computing devices 535 configured to aggregate the sensor data streams from the one or more sensors 505-515 for transmission across one or more communication links to a streaming media server 540. The streaming media server 540 can be configured to received one or more streams of sensor data from the one or more sensors 505-515. A format converter 545 can be coupled to the streaming media server 540 to receive the one or more sensor data streams and convert the sensor data from one format to another. For example, the one or more sensors may generate Motion Picture Expert Group (MPEG) formatted (e.g., H.264) video sensor data, and the format converter 545 can be configured to extract frames of JPEG sensor data. An initial stream processor 550 can be coupled to the format convert 555. The initial stream processor 550 can be configured to segment the sensor data into pre-determined chucks, subdivide the chunks into key frame aligned segment, and create per segment sensor data in one or more formats. For example, the initial stream processor 550 can divide the sensor data into five minute chunks, subdivide the chunks into key frame aligned segment, and convert the key frame aligned segments into MPEG, MPEG Dynamic Adaptive Streaming over Hypertext Transfer Protocol (DASH) format, and or the like. The initial stream processor 550 can be configured to store the sensor stream segments in one or more data structures for storing sensor streams 555. In one implementation, as sensor stream segments are received, each new segment can be appended to the previous sensor stream segments stored in the one or more data structures for storing sensor streams 555.

Figure 6:
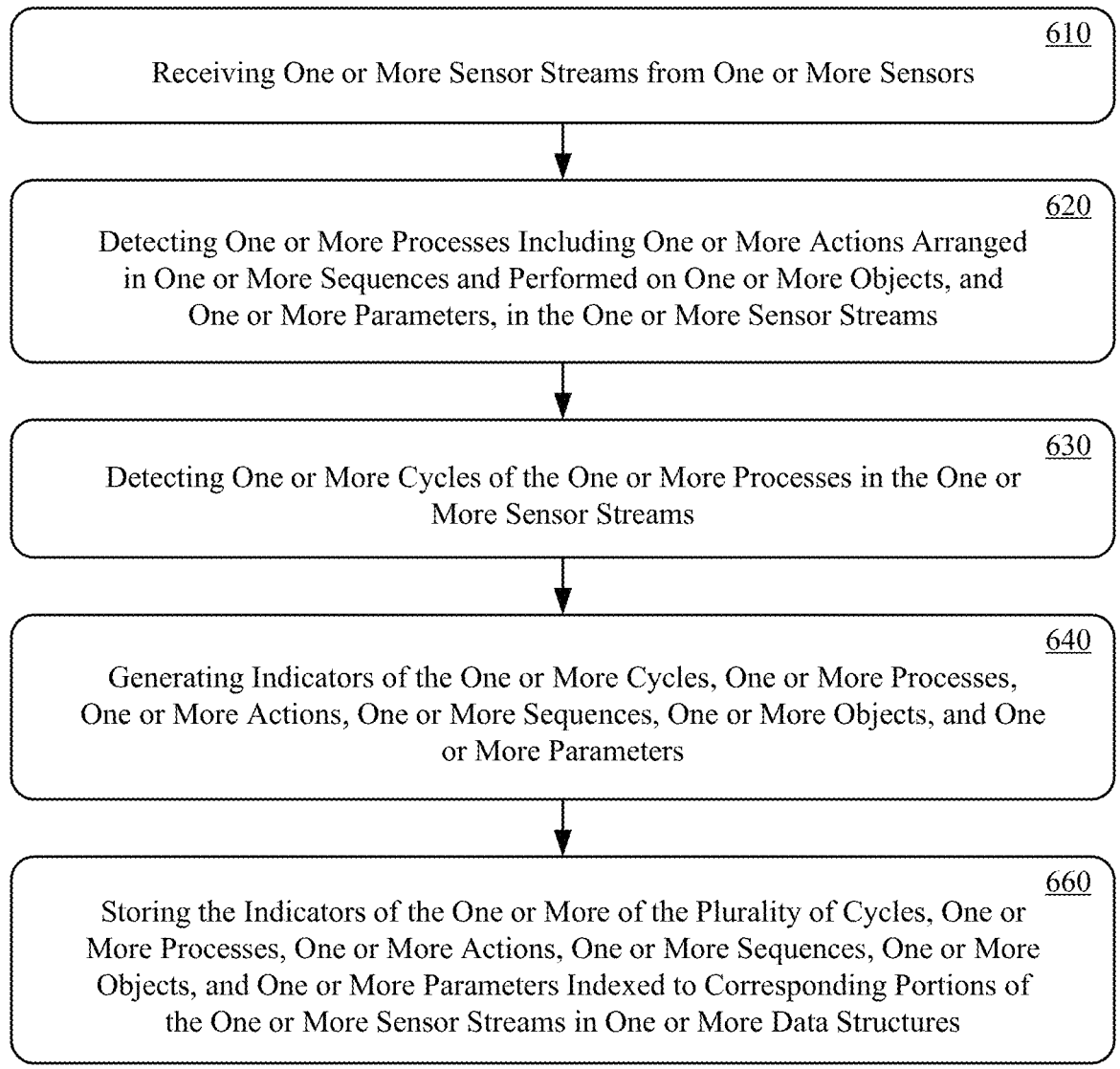
FIG. 6 shows an exemplary method of detecting actions, in accordance with aspects of the present technology.

A stream queue 560 can also be coupled to the format converter 545. The stream queue 560 can be configured to buffer the sensor data from the format converter 545 for processing by the one or more machine learning back-end units 520. The one or more machine learning back-end units 520 can be configured to recognize, in real time, one or more cycles, processes, actions, sequences, objects, parameters and the like in the sensor streams received from the plurality of sensors 505-515. Referring now to FIG. 6, an exemplary method of detecting actions, in accordance with aspects of the present technology, is shown. The action recognition method can include receiving one or more sensor streams from one or more sensors, at 610. In one implementation, one or more machine learning back-end units 520 can be configured to receive sensor streams from sensors 505-515 disposed at one or more stations.

At 620, a plurality of processes including one or more actions arranged in one or more sequences and performed on one or more objects, and one or more parameters can be detected, in the one or more sensor streams. At 630, one or more cycles of the plurality of processes in the sensor stream can also be determined. In one implementation, the one or more machine learning back-end units 520 can recognize cycles, processes, actions, sequences, objects, parameters and the like in sensor streams utilizing deep learning, decision tree learning, inductive logic programming, clustering, reinforcement learning, Bayesian networks, and or the like.

At 640, indicators of the one or more cycles, one or more processes, one or more actions, one or more sequences, one or more objects, and one or more parameters can be generated. In one implementation, the one or more machine learning back-end units 520 can be configured to generate indicators of the one or more cycles, processes, actions, sequences, objects, parameters and or the like. The indicators can include descriptions, identifiers, values and or the like associated with the cycles, processes, actions, sequences, objects, and or parameters. The parameters can include, but is not limited to, time, duration, location (e.g., x, y, z, t), reach point, motion path, grid point, quantity, sensor identifier, station identifier, and bar codes.

At 660, the indicators of the one or more cycles, one or more processes, one or more actions, one or more sequences, one or more objects, and one or more parameters indexed to corresponding portions of the sensor streams can be stored in one or more data structures for storing data sets 565. In one implementation, the one or more machine learning back-end units 520 can be configured to store a data set including the indicators of the one or more processes, one or more actions, one or more sequences, one or more objects, and one or more parameters for each cycle. The data sets can be stored in one or more data structures for storing the data sets 565. The indicators of the one or more cycles, one or more processes, one or more actions, one or more sequences, one or more objects, and one or more parameters in the data sets can be indexed to corresponding portion of the sensor streams in one or more data structures for storing sensor streams 555.

In one implementation, the one or more streams of sensor data and the indicators of the one or more of the plurality of cycles, one or more processes, one or more actions, one or more sequences, one or more objects and one or more parameters indexed to corresponding portion of the one or more streams of sensor data can be encrypted when stored to protect the integrity of the streams of sensor data and or the data sets. In one implementation, the one or more streams of sensor data and the indicators of the one or more of the plurality of cycles, one or more processes, one or more actions, one or more sequences, one or more objects and one or more parameters indexed to corresponding portion of the one or more streams of sensor data can be stored utilizing block chaining. The blockchaining can be applied across the cycles, sensor streams, stations, supply chain and or the like. The blockchaining can include calculating a cryptographic hash based on blocks of the data sets and or blocks of the streams of sensor data. The data sets, streams of sensor data and the cryptographic hash can be stored in one or more data structures in a distributed network.

Referring again to FIG. 5, the one or more analytics units 525 can be coupled to the one or more data structures for storing the sensor streams 555, one or more data structures for storing the data set 565, one or more additional sources of data 570, one or more data structures for storing analytics 575. The one or more analytics units 525 can be configured to perform statistical analysis on the cycle, process, action, sequence, object and parameter data in one or more data sets. The one or more analytics units 525 can also utilize additional data received from one or more additional data sources 570. The additional data sources 570 can include, but are not limited to, Manufacturing Execution Systems (MES), warehouse management system, or patient management system, accounting systems, robot datasheets, human resource records, bill of materials, and sales systems. Some examples of data that can be received from the additional data sources 570 can include, but is not limited to, time, date, shift, day of week, plant, factory, assembly line, sub-assembly line, building, room, supplier, work space, action capability, and energy consumption, ownership cost. The one or more analytics units 525 can be configured to utilize the additional data from one or more additional source of data 570 to update, correct, extend, augment or the like, the data about the cycles, processes, action, sequences, objects and parameters in the data sets. Similarly, the additional data can also be utilized to update, correct, extend, augment or the like, the analytics generate by the one or more analytics front-end units 525. The one or more analytics units 525 can also store trends and other comparative analytics utilizing the data sets and or the additional data, can use sensor fusion to merge data from multiple sensors, and other similar processing and store the results in the one or more data structures for storing analytics 575. In one implementation, one or more engines 170, such as the one or more machine learning back-end units 520 and or the one or more analytics units 525, can create a data structure including a plurality of data sets, the data sets including one or more indicators of at least one of one or more cycles, one or more processes, one or more actions, one or more sequences, one or more object and one or more parameters. The one or more engine 170 can build the data structure based on the one of one or more cycles, one or more processes, one or more actions, one or more sequences, one or more object and one or more parameters detected in the one or more sensor streams. The data structure definition, configuration and population can be performed in real time based upon the content of the one or more sensor streams. For example, Table 1 shows a table defined, configured and populated as the sensor streams are processed by the one or more machine learning back-end unit 520.

TABLE 1

ENTITY ID DATA STUCTURE (TABLE 1)

| FRAME | HUMAN | HAND | ARM | LEG | MOTHER-BOARD | SCREW |
|---|---|---|---|---|---|---|
| 1 | Yes | Yes | Yes | Yes | YES | Yes |
| 2 | Yes | No | No | Yes | Yes | No |
| 3 | Yes | Yes | Yes | Yes | YES | Yes |

The data structure creation process can continue to expand upon the initial structure and or create additional data structures base upon additional processing of the one or more sensor streams.

In one embodiment, the status associated with entities is added to a data structure configuration (e.g., engaged in an action, subject to a force, etc.) based upon processing of the access information. In one embodiment, activity associated with the entities is added to a data structure configuration (e.g., engaged in an action, subject to a force, etc.) based upon processing of the access information. One example of entity status data set created from processing of above entity ID data set (e.g., motion vector analysis of image object, etc.) is illustrated in Table 2.

TABLE 2

ENTITY STATUS DATA STRUCTURE (TABLE 2)

| FRAME | HAND MOVING | ARM MOVING | LEG MOVING | HUMAN MOVING |
|---|---|---|---|---|
| 1 | Yes | Yes | No | Yes |
| 2 | No | No | Yes | No |
| 3 | Yes | Yes | Yes | Yes |

In one embodiment, a third-party data structure as illustrated in Table 3 can be accessed.

TABLE 3

OSHA DATA STRUCTURE (TABLE 3)

| ACTIVITY | SAFE TO MOVE LEG | SAFE TO MOVE HAND |
|---|---|---|
| SCREWING TO MOTHERBOARD | No | Yes |
| LIFTING HOUSING | Yes | Yes |

In one embodiment, activity associated with entities is added to a data structure configuration (e.g., engaged in an action, subject to a force, etc.) based upon processing of the access information as illustrated in Table 4.

TABLE 4

ACTIVITY DATA STRUCTURE (TABLE 4)

| FRAME | SCREWING TO MOTHERBOARD | HUMAN ACTION SAFE | MOTHERBOARD COMPLETE |
|---|---|---|---|
| 1 | Yes | Yes | Yes |
| 2 | No | NA | NO |
| 3 | Yes | NO | Yes |

Table 4 is created by one or more engines 170 based on further analytics/processing of info in Table 1, Table 2 and Table 3. In one example, Table 4 is automatically configured to have a column for screwing to motherboard. In frames 1 and 3 since hand is moving (see Table 2) and screw present (see Table 1), then screwing to motherboard (see Table 3). In frame 2, since hand is not moving (see Table 2) and screw not present (see Table 1), then no screwing to motherboard (see Table 3).

Table 4 is also automatically configured to have a column for human action safe. In frame 1 since leg not moving in frame (see Table 2) the worker is safely (see Table 3) standing at workstation while engage in activity of screwing to motherboard. In frame 3 since leg moving (see Table 2)

the worker is not safely (see Table 3) standing at workstation while engage in activity of screwing to motherboard.

The one or more analytics units 525 can also be coupled to one or more front-end units 580. The one or more front-end units 575 can include a mentor portal 580, a management portal 585, and other similar portals. The mentor portal 550 can be configured for presenting feedback generated by the one or more analytics units 525 and or the one or more front-end units 575 to one or more actors. For example, the mentor portal 580 can include a touch screen display for indicating discrepancies in the processes, actions, sequences, objects and parameters at a corresponding station. The mentor portal 580 could also present training content generated by the one or more analytics units 525 and or the one or more front-end units 575 to an actor at a corresponding station. The management port 585 can be configured to enable searching of the one or more data structures storing analytics, data sets and sensor streams. The management port 585 can also be utilized to control operation of the one or more analytics units 525 for such functions as generating training content, creating work charts, performing line balancing analysis, assessing ergonomics, creating job assignments, performing causal analysis, automation analysis, presenting aggregated statistics, and the like.

The action recognition and analytics system 500 can non-intrusively digitize processes, actions, sequences, objects, parameters and the like performed by numerous entities, including both humans and machines, using machine learning. The action recognition and analytics system 500 enables human activity to be measured automatically, continuously and at scale. By digitizing the performed processes, actions, sequences, objects, parameters, and the like, the action recognition and analytics system 500 can optimize manual and/or automatic processes. In one instance, the action recognition and analytics system 500 enables the creation of a fundamentally new data set of human activity. In another instance, the action recognition and analytics system 500 enables the creation of a second fundamentally new data set of man and machine collaborating in activities. The data set from the action recognition and analytics system 500 includes quantitative data, such as which actions were performed by which person, at which station, on which specific part, at what time. The data set can also include judgements based on performance data, such as does a given person perform better or worse that average. The data set can also include inferences based on an understanding of the process, such as did a given product exited the assembly line with one or more incomplete tasks.

Figure 7:
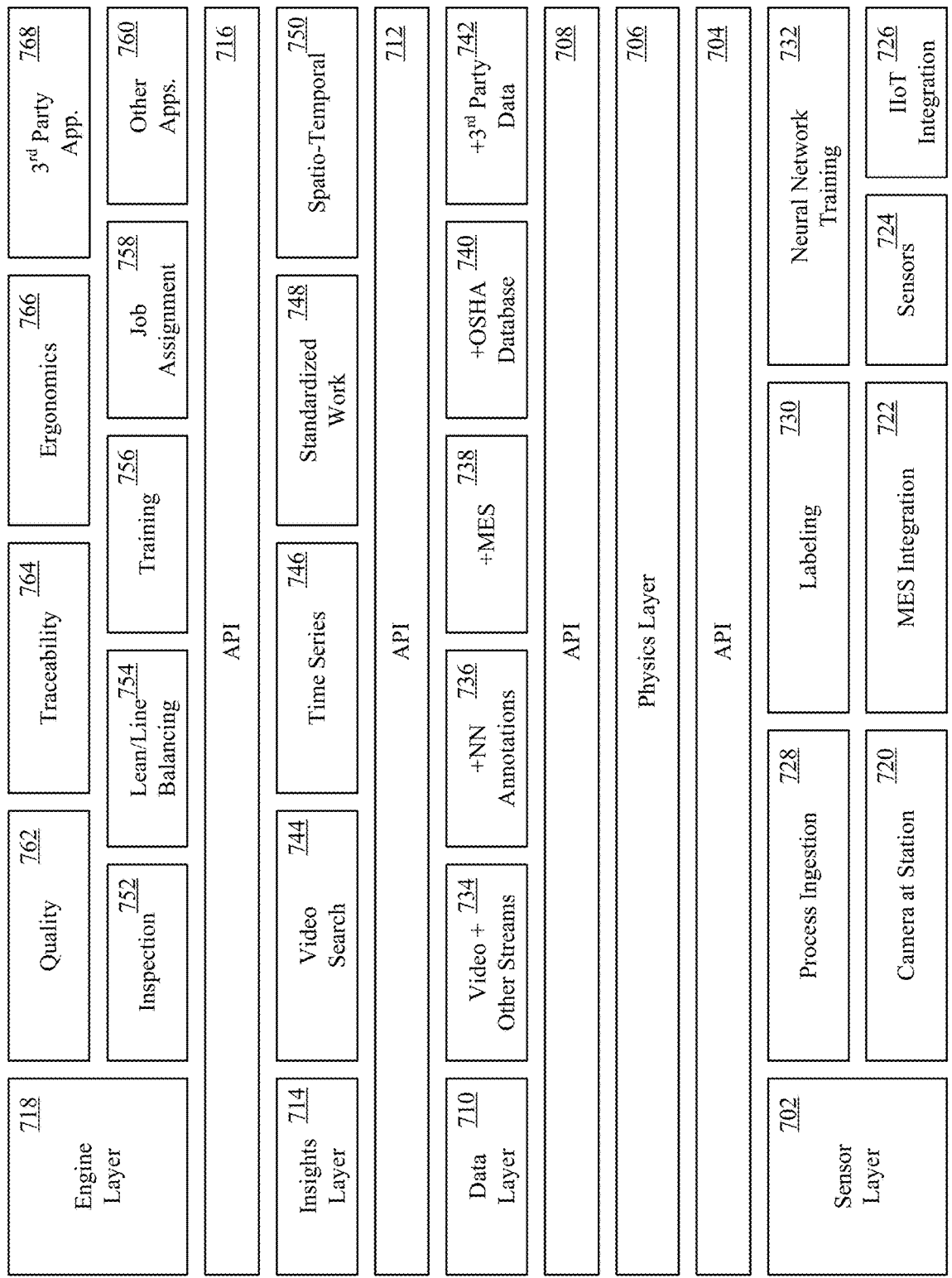
FIG. 7 shows an action recognition and analytics system, in accordance with aspects of the present technology.

Referring now to FIG. 7, an action recognition and analytics system, in accordance with aspects of the present technology, is shown. The action recognition and analytics system can include a plurality of sensor layers 702, a first Application Programming Interface (API) 704, a physics layer 706, a second API 708, a plurality of data 710, a third API 712, a plurality of insights 714, a fourth API 716 and a plurality of engine layers 718. The sensor layer 702 can include, for example, cameras at one or more stations 720, MES stations 722, sensors 724, IIoT integrations 726, process ingestion 728, labeling 730, neural network training 732 and or the like. The physics layer 706 captures data from the sensor layer 702 to passes it to the data layer 710. The data layer 710, can include but not limited to, video and other streams 734, +NN annotations 736, +MES 738, +OSHA database 740, and third-party data 742. The insights layer 714 can provide for video search 744, time series data 746, standardized work 748, and spatio-temporal 750. The engine layer 718 can be utilized for inspection 752, lean/line balancing 754, training 756, job assignment 758, other applications 760, quality 762, traceability 764, ergonomics 766, and third party applications 768.

Figure 8:
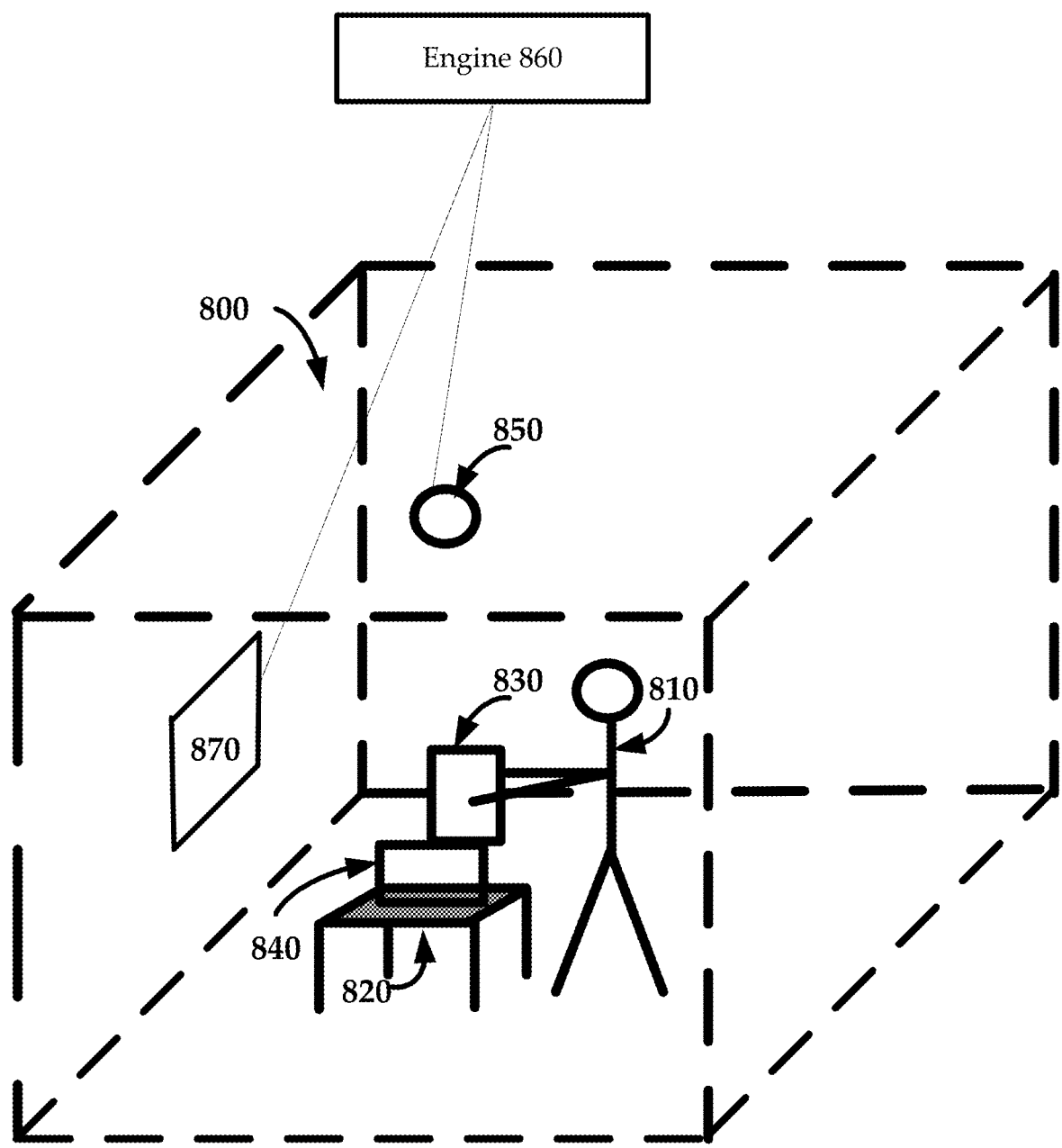
FIG. 8 shows an exemplary station, in accordance with aspects of the present technology.

Referring now to FIG. 8, an exemplary station, in accordance with aspects of the present technology, is shown. The station 800 is an areas associated with one or more cycles, processes, actions, sequences, objects, parameters and or the like, herein also referred to as activity. Information regarding a station can be gathered and analyzed automatically. The information can also be gathered and analyzed in real time. In one exemplary implementation, an engine participates in the information gathering and analysis. The engine can use Artificial Intelligence to facilitate the information gathering and analysis. It is appreciated there can be many different types of stations with various associated entities and activities. Additional descriptions of stations, entities, activities, information gathering, and analytics are discussed in other sections of this detailed description.

A station or area associated with an activity can include various entities, some of which participate in the activity within the area. An entity can be considered an actor, an object, and so on. An actor can perform various actions on an object associated with an activity in the station. It is appreciated a station can be compatible with various types of actors (e.g., human, robot, machine, etc.). An object can be a target object that is the target of the action (e.g., thing being acted on, a product, a tool, etc.). It is appreciated that an object can be a target object that is the target of the action and there can be various types of target objects (e.g., component of a product or article of manufacture, an agricultural item, part of a thing or person being operated on, etc.). An object can be a supporting object that supports (e.g., assists, facilitates, aids, etc.) the activity. There can be various types of supporting objects, including load bearing components (e.g., a work bench, conveyor belt, assembly line, table top etc.), a tool (e.g., drill, screwdriver, lathe, press, etc.), a device that regulates environmental conditions (e.g., heating ventilating and air conditioning component, lighting component, fire control system, etc.), and so on. It is appreciated there can be many different types of stations with a various entities involved with a variety of activities. Additional descriptions of the station, entities, and activities are discussed in other sections of this detailed description.

The station 800 can include a human actor 810, supporting object 820, and target objects 830 and 840. In one embodiment, the human actor 810 is assembling a product that includes target objects 830, 840 while supporting object 820 is facilitating the activity. In one embodiment, target objects 830, 840 are portions of a manufactured product (e.g., a motherboard and a housing of an electronic component, a frame and a motor of a device, a first and a second structural member of an apparatus, legs and seat portion of a chair, etc.). In one embodiment, target objects 830, 840 are items being loaded in a transportation vehicle. In one embodiment, target objects 830, 840 are products being stocked in a retail establishment. Supporting object 820 is a load bearing component (e.g., a work bench, a table, etc.) that holds target object 840 (e.g., during the activity, after the activity, etc.). Sensor 850 senses information about the station (e.g., actors, objects, activities, actions, etc.) and forwards the information to one or more engines 860. Sensor 850 can be similar to sensor 135. Engine 860 can include a machine learning back end component, analytics, and front end similar to machine learning back end unit 180, analytics unit 190, and front end 190. Engine 860 performs analytics on the information and can forward feedback to feedback component 870 (e.g., a display, speaker, etc.) that conveys the feedback to human actor 810.

Figure 9:
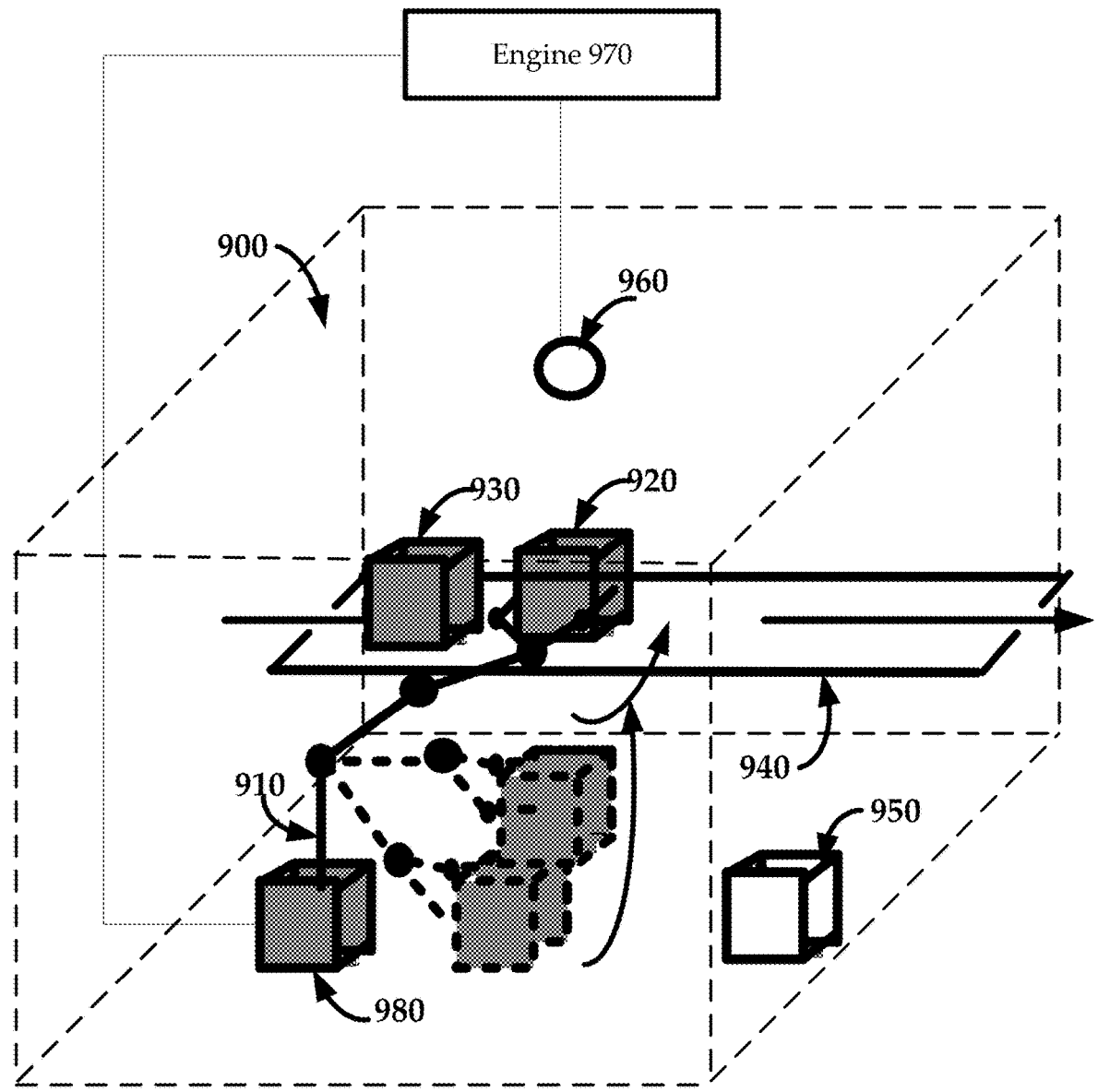
FIG. 9 shows an exemplary station, in accordance with aspects of the present technology.

Referring now to FIG. 9, an exemplary station, in accordance with aspects of the present technology, is shown. The station 900 includes a robot actor 910, target objects 920, 930, and supporting objects 940, 950. In one embodiment, the robot actor 910 is assembling target objects 920, 930 and supporting objects 940, 950 are facilitating the activity. In one embodiment, target objects 920, 930 are portions of a manufactured product. Supporting object 940 (e.g., an assembly line, a conveyor belt, etc.) holds target objects 920, 930 during the activity and moves the combined target object 920, 930 to a subsequent station (not shown) after the activity. Supporting object 940 provides area support (e.g., lighting, fan temperature control, etc.). Sensor 960 senses information about the station (e.g., actors, objects, activities, actions, etc.) and forwards the information to engine 970. Engine 970 performs analytics on the information and forwards feedback to a controller 980 that controls robot 910. Engine 970 can be similar to engine 170 and sensor 960 can be similar to sensor 135.

A station can be associated with various environments. The station can be related to an economic sector. A first economic sector can include the retrieval and production of raw materials (e.g., raw food, fuel, minerals, etc.). A second economic sector can include the transformation of raw or intermediate materials into goods (e.g., manufacturing products, manufacturing steel into cars, manufacturing textiles into clothing, etc.). A third sector can include the supply and delivery of services and products (e.g., an intangible aspect in its own right, intangible aspect as a significant element of a tangible product, etc.) to various parties (e.g., consumers, businesses, governments, etc.). In one embodiment, the third sector can include sub sectors. One sub sector can include information and knowledge-based services. Another sub sector can include hospitality and human services. A station can be associated with a segment of an economy (e.g., manufacturing, retail, warehousing, agriculture, industrial, transportation, utility, financial, energy, healthcare, technology, etc.). It is appreciated there can be many different types of stations and corresponding entities and activities. Additional descriptions of the station, entities, and activities are discussed in other sections of this detailed description.

Figure 10:
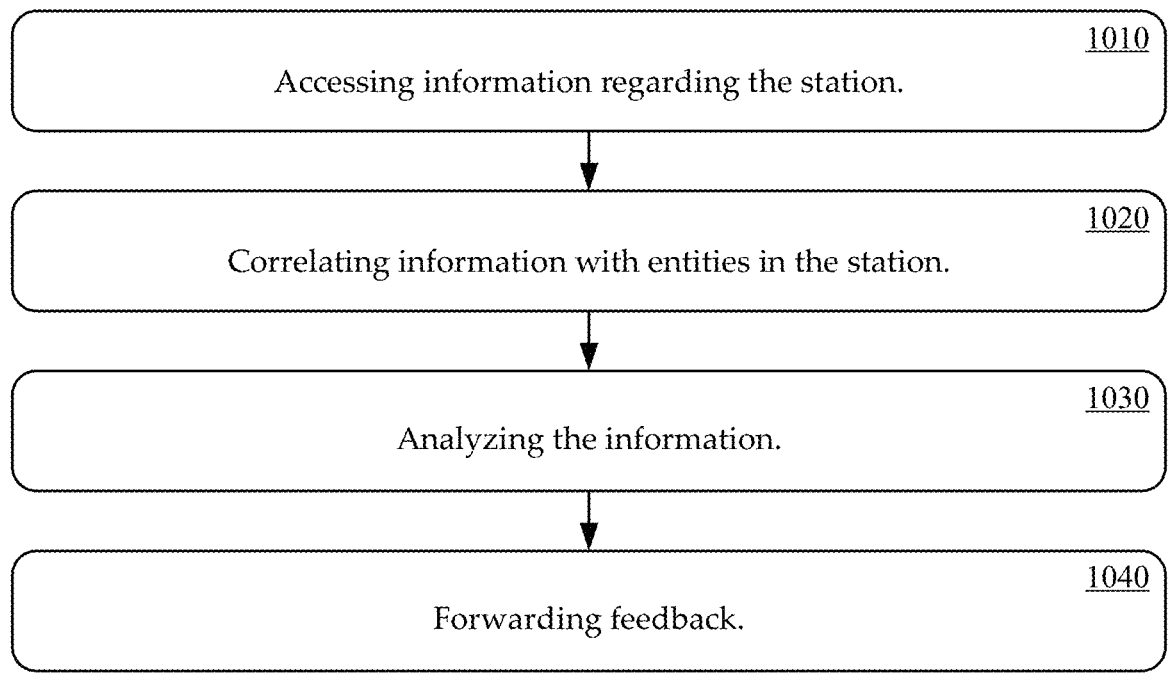
FIG. 10 shows an exemplary station activity analysis method, in accordance with one embodiment.

In one embodiment, station information is gathered and analyzed. In one exemplary implementation, an engine (e.g., an information processing engine, a system control engine, an Artificial Intelligence engine, etc.) can access information regarding the station (e.g., information on the entities, the activity, the action, etc.) and utilizes the information to perform various analytics associated with the station. In one embodiment, engine can include a machine learning back end unit, analytics unit, front end unit, and data storage unit similar to machine learning back end 180, analytics 185, front end 190 and data storage 175. In one embodiment, a station activity analysis process is performed. Referring now to FIG. 10, an exemplary station activity analysis method, in accordance with one embodiment, is shown.

At 1010, information regarding the station is accessed. In one embodiment, the information is accessed by an engine. The information can be accessed in real time. The information can be accessed from monitors/sensors associated with a station. The information can be accessed from an information storage repository. The information can include various types of information (e.g., video, thermal, optical, etc.). Additional descriptions of the accessing information are discussed in other sections of this detailed description At 1020, information is correlated with entities in the station and optionally with additional data sources. In one embodiment, the information the correlation is established at least in part by an engine. The engine can associate the accessed information with an entity in a station. An entity can include an actor, an object, and so on. Additional descriptions of the correlating information with entities are discussed in other sections of this detailed description.

At 1030, various analytics are performed utilizing the accessed information at 1010, and correlations at 1020. In one embodiment, an engine utilizes the information to perform various analytics associated with station. The analytics can be directed at various aspects of an activity (e.g., validation of actions, abnormality detection, training, assignment of actor to an action, tracking activity on an object, determining replacement actor, examining actions of actors with respect to an integrated activity, automatic creation of work charts, creating ergonomic data, identify product knitting components, etc.) Additional descriptions of the analytics are discussed in other sections of this detailed description.

At 1040, optionally, results of the analysis can be forwarded as feedback. The feedback can include directions to entities in the station. In one embodiment, the information accessing, analysis, and feedback are performed in real time. Additional descriptions of the station, engine, entities, activities, analytics and feedback are discussed in other sections of this detailed description, It is also appreciated that accessed information can include general information regarding the station (e.g., environmental information, generic identification of the station, activities expected in station, a golden rule for the station, etc.). Environmental information can include ambient aspects and characteristics of the station (e.g., temperature, lighting conditions, visibility, moisture, humidity, ambient aroma, wind, etc.).

It also appreciated that some of types of characteristics or features can apply to a particular portion of a station and also the general environment of a station. In one exemplary implementation, a portion of a station (e.g., work bench, floor area, etc.) can have a first particular visibility level and the ambient environment of the station can have a second particular visibility level. It is appreciated that some of types of characteristics or features can apply to a particular entity in a station and also the station environment. In one embodiment, an entity (e.g., a human, robot, target object, etc.) can have a first particular temperature range and the station environment can have a second particular temperature range.

The action recognition and analytics system 100, 500 can be utilized for process validation, anomaly detection and/or process quality assurance in real time. The action recognition and analytics system 100, 500 can also be utilized for real time contextual training. The action recognition and analytics system 100, 500 can be configured for assembling training libraries from video dips of processes to speed new product introductions or onboard new employees. The action recognition and analytics system 100, 500 can also be utilized for line balancing by identifying processes, sequences and/or actions to move among stations and implementing lean processes automatically. The action recognition and analytics system 100, 500 can also automatically create standardized work charts by statistical analysis of processes, sequences and actions. The action recognition and analytics system 100, 500 can also automatically create birth certificate videos for a specific unit. The action recognition and analytics system 100, 500 can also be utilized for automatically creating statistically accurate ergonomics data. The action recognition and analytics system 100, 500 can also be utilized to create programmatic job assignments based on skills, tasks, ergonomics and time. The action recognition and analytics system 100, 500 can also be utilized for automatically establishing traceability including for causal analysis. The action recognition and analytics system 100, 500 can also be utilized for kitting products, including real time verification of packing or unpacking by action and image recognition. The action recognition and analytics system 100, 500 can also be utilized to determine the best robot to replace a worker when ergonomic problems are identified. The action recognition and analytics system 100, 500 can also be utilized to design an integrated line of humans and cobot and/or robots. The action recognition and analytics system 100, 500 can also be utilized for automatically programming robots based on observing non-modeled objects in the work space.

Programmatic Job Assignment Based on Skills, Tasks, Ergonomics and Time

A longstanding problem in the field of employee management is the need to assign workers to tasks in a way that optimizes efficiency. The assignment problem as it is known has been traditionally described as assigning J (a set of jobs) to W (a set of workers) so that each worker performs only one job and each job is assigned to only one worker-all while minimizing the cost, as defined by the nature of the business problem. Costs might include worker wages, time to deliver the product to the customer, product quality, and combinations of these cost functions.

Table 5 illustrates a simple example of the Assignment Problem, where 4 Jobs need to be assigned to 4 workers and worker's ability to perform the job is known.

TABLE 5

|  | Job P | Job Q | Job R | Job S |
|---|---|---|---|---|
| Worker A | 7 mins | 2 mins | 8 mins | 5 mins |
| Worker B | 6 mins | 4 mins | 3 mins | 2 mins |
| Worker C | 1 mins | 4 mins | 4 mins | 3 mins |
| Worker D | 8 mins | 5 mins | 3 mins | 2 mins |

The assignment problem has traditionally been solved as a linear programming problem using the Simplex method (and derivatives of this like the Hungarian method) to do so efficiently in programming environments like Matlab. However, existing formulations for determining employee assignments dramatically simplify the realities of life by assuming that the workers have robot-like properties, and that those properties do not change on a temporal basis. The real-world is fundamentally variable—with changes being introduced every minute and on every shift—and measuring these changes is imprecise. This fundamental variance is rarely explicitly modeled in the assignment process.

Accordingly, embodiments of the present invention continually measure aspects of the real-world, making it possible to describe the performance of an actor (e.g., a human worker or robot) as a distribution function that reflects variations in performance over time. By using a vastly more detailed data set, embodiments of the present invention apply more relevant versions of mathematical programming techniques to more efficiently assign actors to actions. For example, parallel representations or multi-stage optimization techniques may be used to solve the multi-objective problem while finding optimal solutions to the expected cost functions.

In one example, for a set of m workers $w_0, w_1, \ldots w_m$ and a set of n tasks $t_0, t_1, \ldots, t_n$, assigning a task $t_j$ to worker $w_i$ has a cost $C_{ij}$. A computer implemented sequence of steps automatically determines optimal assignments so that the total cost is minimized. This problem maps to the maximum weighted bipartite matching problem in graphs. There are two sets of vertices corresponding to workers and tasks respectively. Weighted edges run between each worker and each edge. Thus there are m×n edges. The weight of an edge between worker i and task i is $1/C_{ij}$. The maximum edge weight (equivalently minimum cost) solution can be obtained via the Hungarian algorithm.

A neural network may be used to analyze factory floor sensor streams (e.g., videos) to estimate aggregate action completion times for each worker and each action. Using these estimates, estimates for cost (CO) of assigning task j to worker i can be determined. This cost has two aspects. First, the competence mismatch takes the average (over all observations) completion time for task j taken by worker i relative to the same over all workers. In general, the larger the time taken by a worker to complete a task, the more mismatched the worker is to the task. The ergonomics cost is a second aspect of the cost $C_{ij}$, where each task has an associated effort estimate. This can be estimated as the average completion time for the specific task over all workers, relative to the average completion time of all task over all workers. Each worker has a fatigue score which is the sum of the effort V required for all recent tasks.

For example, one exemplary process of assigning task j to worker i involves the following equations in Table 6:

TABLE 6 tijk = time taken by worker i to complete a task j on observation k $\bar{t}_{ij} = \sum_{\forall k} t_{ijk}$ = average completion time of task j by worker i $c(i, j) = \dfrac{\bar{t}_{ij}}{\dfrac{1}{N}\sum_{i=1}^{} \bar{t}_{ij}}$ = competence mismatch cost $\dfrac{\sum_{\forall i} \bar{t}_{ij}}{\sum_{\forall i,j} \bar{t}_{ij}}$ = effort required for task j $\sum_{\forall recent\ tasks\ j\ by\ worker\ i}$ effort required for task j = fatigue score for worker i Effort required for task j × fatigue score for worker i = ergonomic cost e(i, j)

$c(i, j) = \alpha c(i, j) + (1 - \alpha)e(i, j)$, where $0 \leq \alpha \leq 1$; $\alpha \to$ relative importance between competence mismatch and ergonomics.

According to some embodiments, the problem of assigning resources (e.g., actors) to actions or processes is represented by a linear cost function with linear constraints, and embodiments of the present invention automatically optimize the cost function based on observed data to optimize the cost function in real-time. According to some embodiments, there are more actors than works stations, and the actors are assigned to work stations in shifts where actors rotate through the stations in an optimized manner. Moreover, embodiments of the present invention can consider seniority, actor skill level, actor certification, physical characteristics of actors, quality of work associated with the actor, actor ergonomics, actor endurance or physical fitness, the speed at which an actor completes tasks, and worker compensation (e.g., overtime, difference in wages, etc.). Furthermore, embodiments of the present invention can certify actors based on the observed skill level, the ergonomics, and the speed at which an actor completes tasks, and certified actors may be prioritized over the non-certified actors.

According to some embodiments, actors include both human workers and robots working side-by-side. It is appreciated that robots do not tire as humans do, the actions of robots are more repeatable than humans, and robots are unable to perform some tasks that humans can perform.

Figure 11:
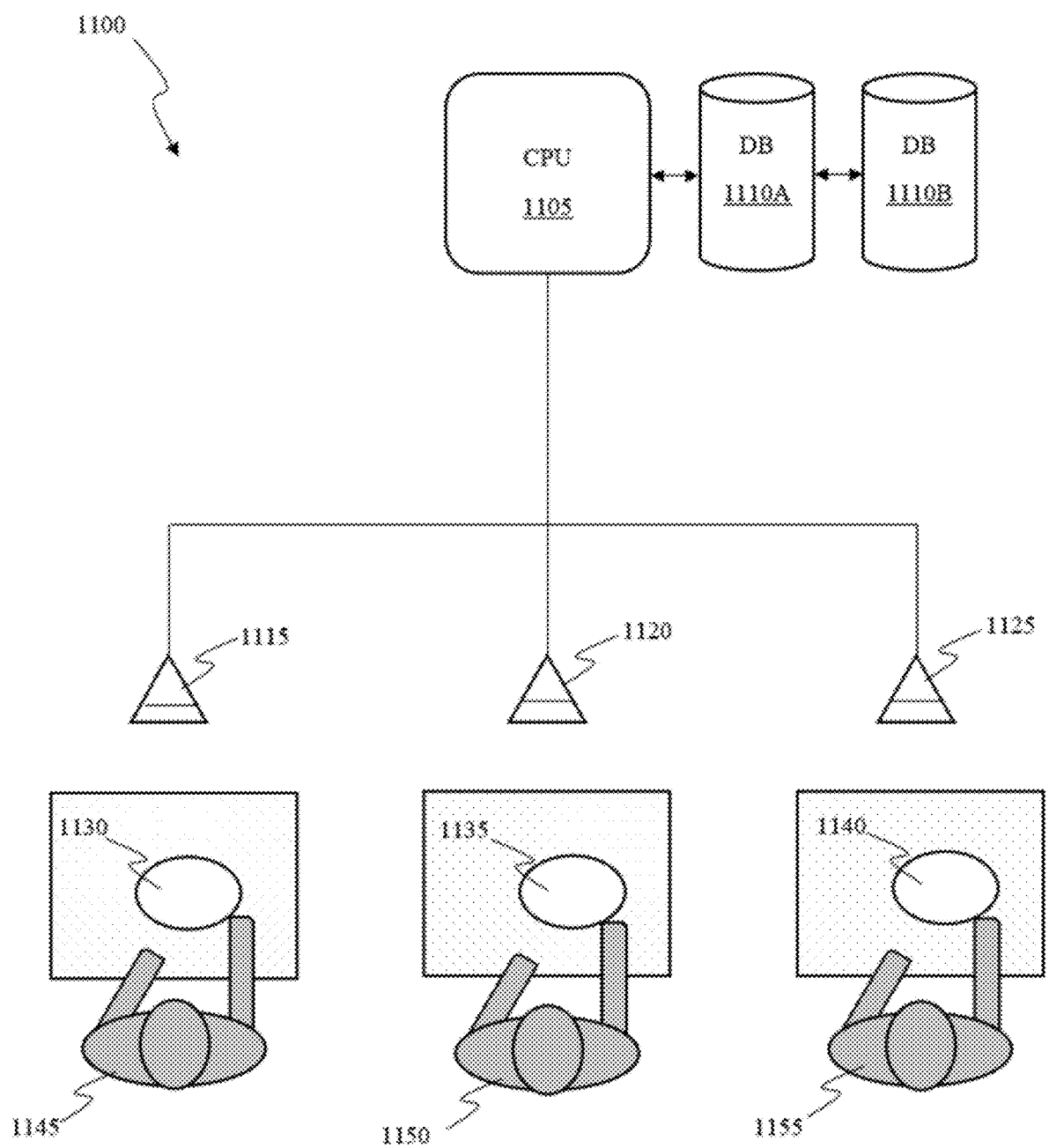
FIG. 11 shows an exemplary computer system for automatically observing and analyzing actions of an actor based on data previously captured by one or more sensors in accordance with various embodiments of the present disclosure.

With regard to FIG. 11, an exemplary computer system 1100 for automatically observing and analyzing actions (e.g., a task or activity) of an actor (e.g., a human worker or robot) based on data previously captured by one or more sensors is depicted according to that described herein with reference to the engine, but is not limited to such. According to an exemplary manufacturing implementation, a plurality of stations 1130-1140 may represent different work stations along an assembly line. One or more sensors 1115-1125 can be disposed non-intrusively at various positions around one or more of the stations 1130-1140. The same set of one or more sensors 1115-1125 can be disposed at each station 1130-1140, or different sets of one or more sensors 1115-1125 can be disposed at different stations 1130-1140.

The sensors 1115-1125 can include one or more sensors such as video cameras, thermal imaging sensors, depth sensors, or the like. The sensors 1115-1125 can also include one or more other sensors, such as audio, temperature, acceleration, torque, compression, tension, or the like sensors. Sensor data is processed by CPU 1105, and one or more databases store data structures including, for example, one or more sensor data streams received from the one or more sensors 1115-1125. Database 1110A depicted in FIG. 11 can include one or more data structures for storing detected cycles, processes, actions, sequences, objects, and parameters thereof indexed to corresponding portions of the one or more sensor streams in the sensor stream data structure. The engine back-end unit 180 and/or the analytics unit 185 depicted in FIG. 1 can store the sensor data streams from the one or more sensors 1115-1125 in the database 1110A for storing the one or more sensor data streams by appending the currently received portion of the sensor data streams to the previous portions of the sensor data streams stored in the database 1110A. The engine back-end unit 180 and/or the analytics unit 185 can also store identifiers of the detected cycles, processes, actions, sequences, objects, and parameters thereof indexed to corresponding portions of the current one or more sensor data streams, for example, in database 1110B.

Figure 17:
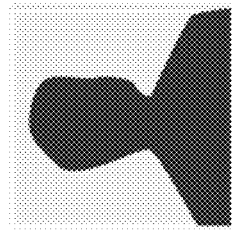
FIG. 17 shows an exemplary worker profile and certificates according to embodiments of the present invention.

The sensors 1115-1125 may be configured to continuously monitor the activities of actors 1145-1155, and the data captured by the sensors 1115-1125 can be described according to a distribution function to reflect variations in performance or steps of a process. For example, the sensor data may be provided in a sensor stream including video frames, thermal sensor data, force sensor data, audio sensor data, and/or light sensor data. In this way, embodiments of the present invention are able to apply relevant mathematical programming techniques (e.g., parallel representations or multi-stage optimization techniques) to efficiently assign actors to specific actions. For example, an actor's performance (e.g., actors 1145-1155) may be tracked over time using sensors 1115-1125 to determine/characterize the actor's skill level, the time spent at various stations, the availability of the actor, and/or the actor's physical/ergonomic ability, and mathematical programming techniques may be applied to the sensor data to efficiently assign the actor to an action. The sensor data capturing the actor's performance may by analyzed to determine if the actor is performing better or worse than average, or to determine the actor's competence level in performing actions, such as determining that a product exited the line with incomplete tasks due to a failure of the worker. The task may include performing an atomic or molecular task on an object 1130-1140, for example. According to some embodiments, the actors 1145-1155 are certified according to a worker profile and certificate as depicted in FIG. 17.

Figure 12:
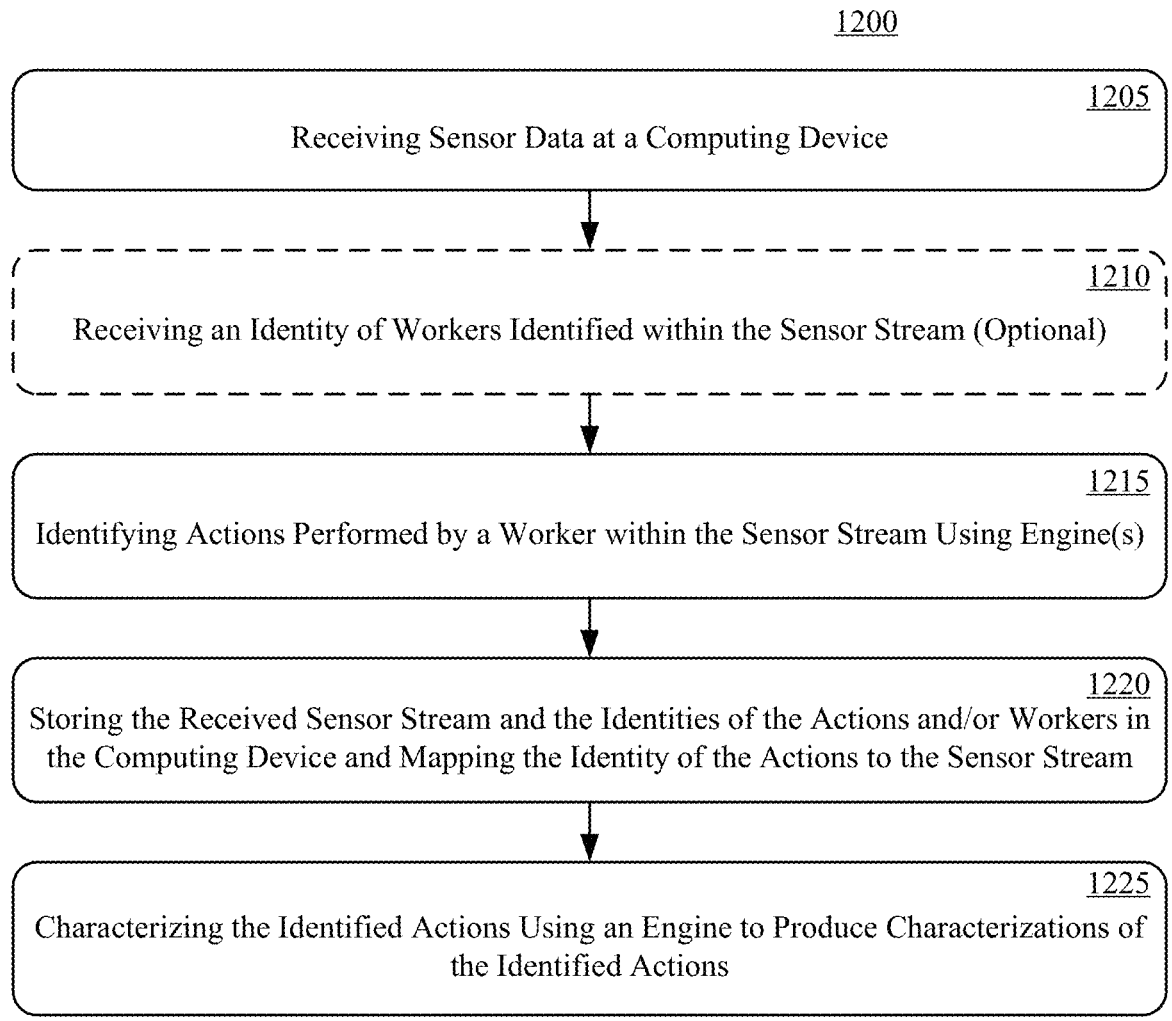
FIG. 12 show a flow chart depicting an exemplary sequence of computer implemented steps for automatically observing and analyzing actor activity in real-time in accordance with various embodiments of the present disclosure.

With regard to FIG. 12, an exemplary sequence of computer implemented steps 1200 for automatically observing and analyzing actor (e.g., worker) activity based on observed data (e.g., video frames, thermal sensor data, force sensor data, audio sensor data, and/or light sensor data) is depicted according to embodiments of the present invention. In the embodiment of FIG. 12, it is assumed that actors are assigned to a fixed station, and each station performs a fixed task. At step 1205, sensor data is received at a computing device. The sensor stream includes sensor information obtained from a sensor operable to sense progress of a work task. Step 1210 may optionally be performed according to some embodiments to receive an identity of actors identified within the sensor stream at the computing device. At step 1215, actions performed by an actor that have been recorded within the sensor stream are identified using one or more engines executed by the computing device. At step 1220, the received sensor stream and identities of the recorded actions are stored in the computing device, and the identity of the actions are mapped to the sensor stream. If step 810 was performed to receive an identity of actors identified within the sensor stream, step 820 may also include storing the identity of the actors in the computing device. At step 1225, the identified actions performed by the actor are characterized by the one or more engines to produce characterizations for the identified actions. The characterizations may include ergonomics of the actor, a skill level of the actor, and/or a time required for the actor to perform the identified actions.

Figure 13:
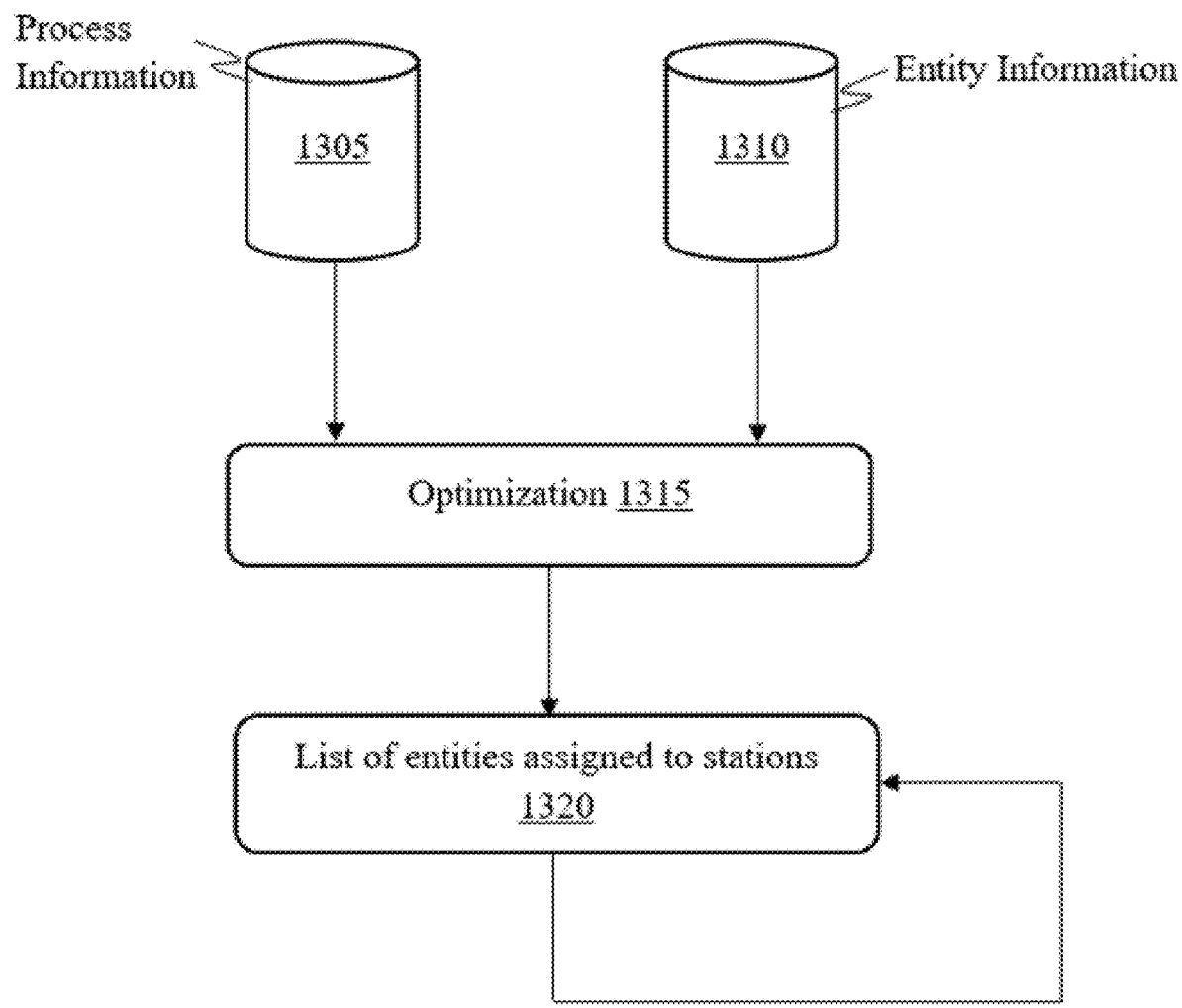
FIG. 13 shows a block diagram and data flow diagram of an exemplary computer system that automatically assigns processes or actions to actors in real-time based on observed data in accordance with various embodiments of the present disclosure.

With regard to FIG. 13, a block diagram and data flow diagram 1300 of an exemplary computer system that automatically assigns processes or actions (e.g., tasks) to actors (e.g., human workers or robots) in real-time based on observed data (e.g., video frames, thermal sensor data, force sensor data, audio sensor data, and/or light sensor data) is depicted according to embodiments of the present invention. In the embodiment of FIG. 13, it is assumed that actors are assigned to a fixed station, and each station performs a fixed task. The computer system stores and/or receives information including process information 1305 and actor information 1310 which may be stored in one or more data structures.

Processes information 1305 includes a list of processes to be performed and characteristics thereof. Actor information 1310 may include a list of actors available to perform actions and optionally characteristics of the actors. Based on the process information 1305 and the actor information 1310, an optimization step 1315 automatically determines which actor to assign to which task and for how long the task should be performed by the actor to generate list 1320. For example, the optimization step 1315 may include solving one or more cost functions with associated constraints to determine the list of actors assigned to stations. The optimization step 1315 may include determining a job assignment to an actor based on the quality of the work of the operator at a specific station, the speed of the operator at a specific station, the cumulative ergonomic load on the operator for that given period of time (e.g., a day) across one or more stations. According to some embodiments, the optimization step 1315 uses one or more equations depicted in Table 6 to determine a list of entities assigned to stations 1320. The list of actors assigned to stations 1320 is updated in real-time as new shifts of actors arrive or as actors tire over time. According to some embodiments, the entity information includes worker profile and certificates as depicted in FIG. 17.

Figure 14:
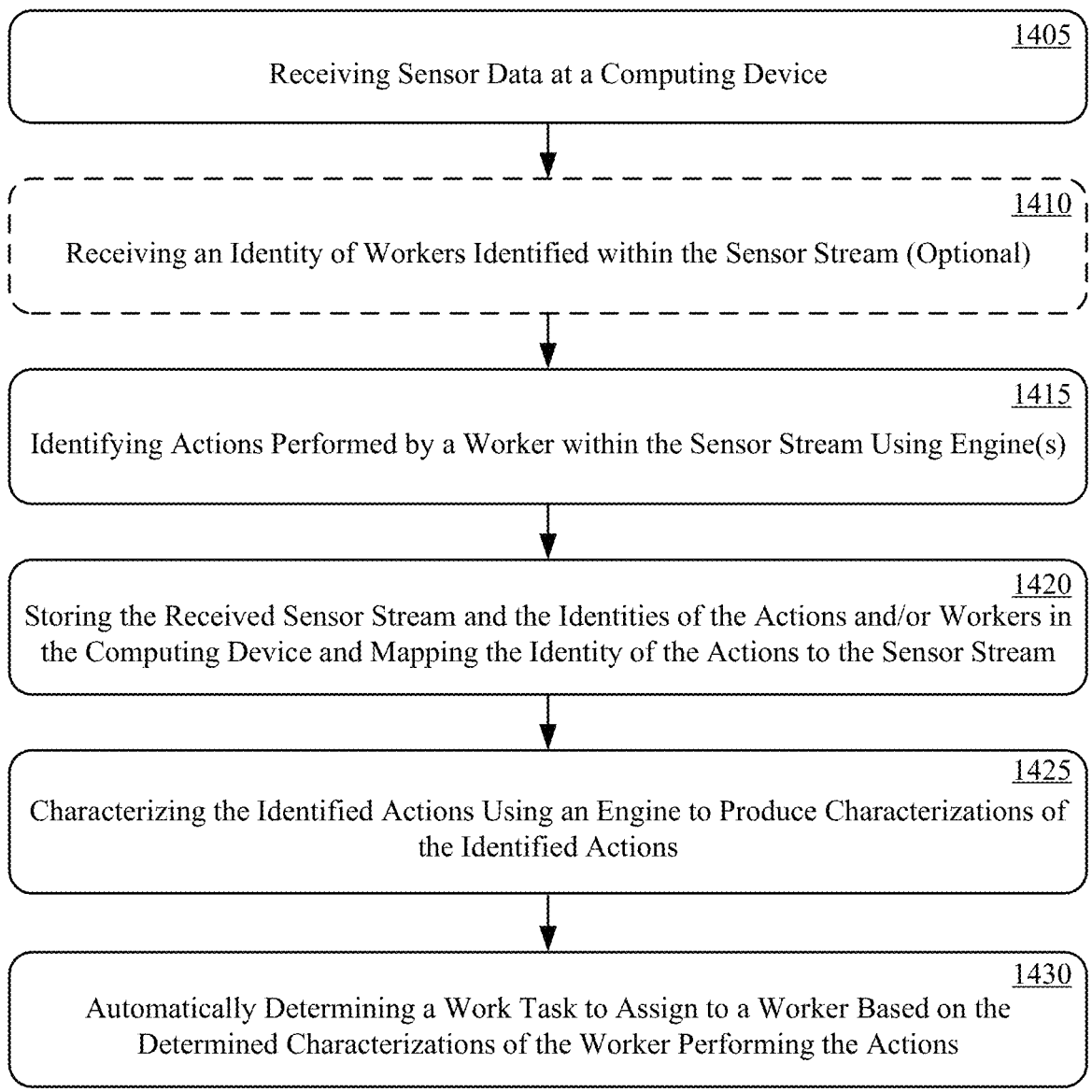
FIG. 14 shows a flow chart depicting an exemplary sequence of computer implemented steps for automatically observing actor activity and assigning processes or actions to actors in real-time based on observed data in accordance with various embodiments of the present disclosure.

With regard to FIG. 14, an exemplary sequence of computer implemented steps 1400 for automatically observing actor activity and assigning processes or actions (e.g., tasks) to actors (e.g., human workers or robots) in real-time based on observed data (e.g., video frames, thermal sensor data, force sensor data, audio sensor data, and/or light sensor data) is depicted according to embodiments of the present invention. The steps 1400 may be performed using one or more equations of Table 6 automatically by a processor of a computer system. In the embodiment of FIG. 14, it is assumed that tasks/actions can be moved from one station to another. At step 1405, sensor data is received at a computing device. The sensor stream includes sensor information obtained from a sensor operable to sense progress of a work task or processes. Step 1410 may optionally be performed according to some embodiments to receive an identity of actors identified within the sensor stream at the computing device. At step 1415, actions performed by an actor that have been recorded within the sensor stream are identified using one or more engines executed by the computing device. At step 1420, the received sensor stream and identity of the recorded actions are stored in the computing device, and the identity of the actions are mapped to the sensor stream. If step 1410 was performed to receive an identity of actors identified within the sensor stream, step 1420 may also include storing the identity of the actors in the computing device.

At step 1425, the identified actions performed by the actor are characterized by the one or more engines to produce characterizations for the identified actions. The characterizations may include ergonomics of the actor, a skill level of the actor, and/or a time required for the actor to perform the identified actions. At step 1430, based on the determined characterizations of the actor performing the actions, an action (e.g., work task) or processes assignment is dynamically determined for the actor in real-time. Step 1430 may include assignment to an actor based on one or more data structures including processes information, a list of actors to assign, and a list of tasks or processes to assign to stations or actors, for example. According to some embodiments, the determined characterizations are used to determine if an actor is certified to a standard. Step 1430 may include moving an actor from one station/task to another station/task, and step 1430 may be repeated over-time to automatically optimize the assignment of actors to tasks based on real-time observations of actor performance.

Figure 15:
FIG. 15 shows an exemplary job assignment input user interface according to embodiments of the present invention.

Referring now to FIG. 15, an exemplary job assignment input user interface 1500 is depicted according to embodiments of the present invention. The job assignment user interface 1500 receives actor line input 1505 and actor shift input 1510 for a list of available associates 1515. For example, the actor line input 1505 may be used to select a specific group or line or actors, and the actor shift input 1510 may be used to select a specific time for assigning jobs. The assign button 1520 is selected to execute a computer-implement job assignments method as described herein according to embodiments of the present invention to generate a job assignments output as depicted in FIG. 16.

Referring now to FIG. 16, an exemplary job assignment output 1600 is depicted according to embodiments of the present invention. The job assignment output 1600 is generated using a computer-implemented job assignment method as described herein according to embodiments of the present invention. The output 1600 includes a list of associates 1605 assigned to station assignment 1610. The list of associates 1605 further includes actor skill levels indicating a good fit, an average fit, a bad fit, or not enough data to determine a skill level. The actor skill level (e.g., associate skill level 1605, station assignment 1610, skill fit 1615, station fit 1620, and ergonomic fit 1625) may be determined according to one or more equations depicted in Table 6.

Referring now to FIG. 17, an exemplary worker profile, in accordance with aspects of the present technology, is shown. The proficiency of a worker can be measured during the contextual training and reported to one or more additional data sources. In one implementation, the one or more engines 170 can report one or more parameters measured during the contextual training to an employee management system for use in a worker profile. In another implementation, the action recognition and analytics system 100, 500 can also utilize the one or more parameters measured during the contextual training for line balancing, programmatic job assignments, and other similar functions.

Figure 18:
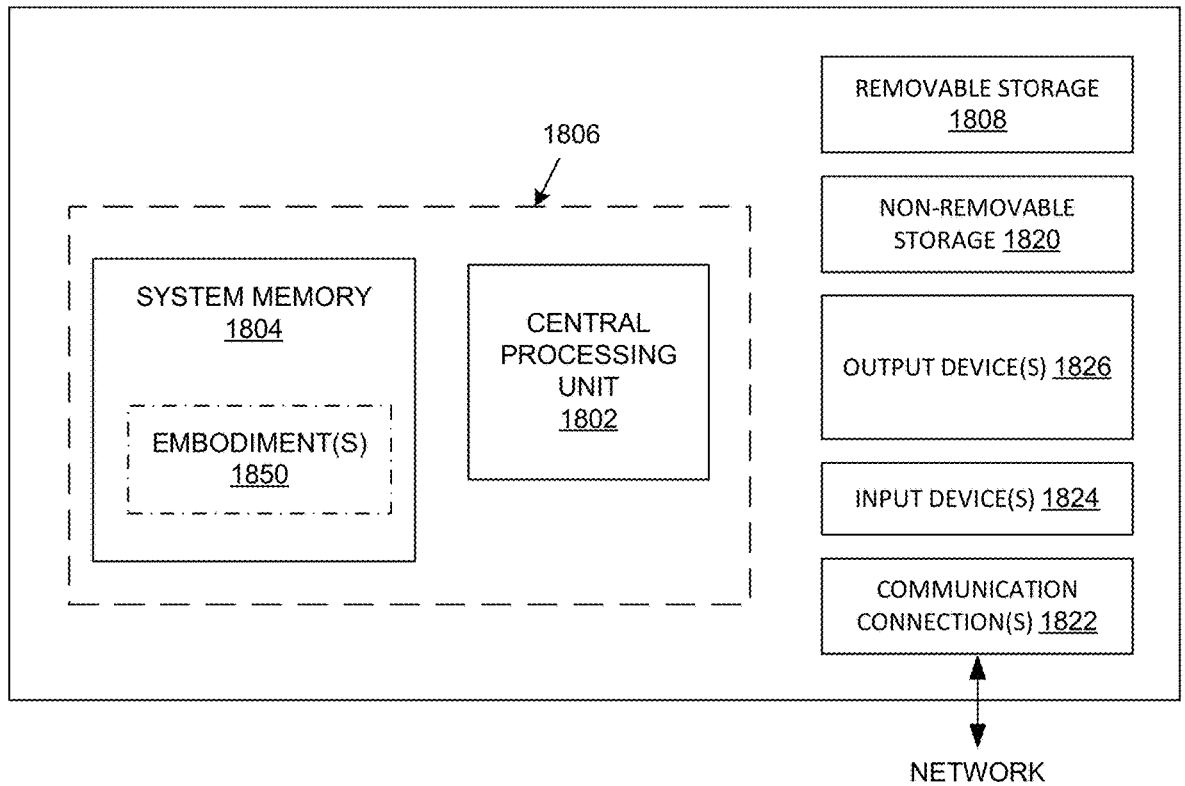
FIG. 18 shows a block diagram of an example of a computing system upon which one or more various embodiments described herein may be implemented in accordance with various embodiments of the present disclosure.

FIG. 18 shows a block diagram of an example of a computing system 1800 upon which one or more various embodiments described herein may be implemented in accordance with various embodiments of the present disclosure. The computer system 1800 may include a cloud-based computer system, a local computer system, or a hybrid computer system that includes both local and remote devices. In a basic configuration, the system 1800 includes at least one processing unit 1802 and memory 1804. This basic configuration is illustrated in FIG. 18 by dashed line 1806. The system 1800 may also have additional features and/or functionality. For example, the system 1800 may also include additional storage (e.g., removable and/or non-removable) including, but not limited to, magnetic or optical disks or tape. Such additional storage is illustrated in FIG. 18 by removable storage 1808 and non-removable storage 1820.

The system 1800 may also contain communications connection(s) 1822 that allow the device to communicate with other devices, e.g., in a networked environment using logical connections to one or more remote computers. Furthermore, the system 1800 may also include input device(s) 1824 such as, but not limited to, a voice input device, touch input device, keyboard, mouse, pen, touch input display device, etc. In addition, the system 1800 may also include output device(s) 1826 such as, but not limited to, a display device, speakers, printer, etc.

In the example of FIG. 18, the memory 1804 includes computer-readable instructions, data structures, program modules, and the like associated with one or more various embodiments 1850 in accordance with the present disclosure. However, the embodiment(s) 1850 may instead reside in any one of the computer storage media used by the system 1800, or may be distributed over some combination of the computer storage media, or may be distributed over some combination of networked computers, but is not limited to such.

It is noted that the computing system 1800 may not include all of the elements illustrated by FIG. 18. Moreover, the computing system 1800 can be implemented to include one or more elements not illustrated by FIG. 18. It is pointed out that the computing system 1800 can be utilized or implemented in any manner similar to that described and/or shown by the present disclosure, but is not limited to such.

The foregoing descriptions of various specific embodiments in accordance with the present disclosure have been presented for purposes of illustration and description. They are not intended to be exhaustive or to limit the present disclosure to the precise forms disclosed, and many modifications and variations are possible in light of the above teaching. The present disclosure is to be construed according to the Claims and their equivalents.

What is claimed is:

1. A computer implemented method of automatically determining work task assignments comprising:
    using a computing device executing a machine learning engine, determining one or more cycles, one or more processes, one or more actions, one or more sequences, one or more objects and one or more parameters by convolution neural network deep learning from one or more video frame sensor streams at one or more manufacturing stations across an assembly line, the determining comprising:
        performing, with a frame feature extractor, a two-dimensional convolution operation on the one or more video frame sensor streams to generate a two-dimensional array of feature vectors;
        determining, with a region of interest detector unit, a dynamic region of interest in the one or more video frame sensor streams, wherein the region of interest detector unit and the frame feature extractor share layers of the convolution neural network;
        processing, with a long short term memory, an area of the one or more video frame sensor streams within the dynamic region of interest without processing an area of the one or more video frame sensor streams outside the dynamic region of interest;
    using the computing device executing the machine learning engine, identifying a plurality of work tasks performed by a plurality of human actors at the plurality of manufacturing stations based on the determined one or more cycles, one or more processes, one or more actions, one or more sequences, one or more objects and one or more parameters;
    using the computing device, determining work task assignments of the plurality of work tasks identified from the one or more video frame sensor streams for the plurality of human actors;
    outputting the work task assignments of the plurality of work tasks to the plurality of human actors for the performance of further cycles of the plurality of work tasks at the plurality of manufacturing stations across the assembly line;
    using the computing device executing the machine learning engine, identifying changes of one or more of the plurality of human actors, the plurality of work tasks, and performance of the plurality of work tasks by the plurality of human actors, in real time;
    using the computing device executing the machine learning engine, updating the work task assignments based on the identified changes of one or more of the plurality of human actors, the plurality of work tasks, and performance of the plurality of work tasks by the plurality of human actors; and
    outputting the updated work task assignments to the plurality of human actors.

2. The method of claim 1, further comprising:
    using the computing device executing the machine learning engine, determining characterizations of the plurality of work tasks performed by the plurality of human actors including ergonomics of each of the plurality of human actors performing the plurality of work tasks; and
    using the computing device executing, further determining the work task assignments based on the determined characterizations.

3. The method of claim 1, further comprising:
    using the computing device executing the machine learning engine, determining characterizations of the plurality of work tasks performed by the plurality of human actors including a skill level of one or more of the plurality of human actors used to perform one or more of the plurality of work tasks; and
    using the computing device, further determining the work task assignments based on the determined characterizations.

4. The method of claim 1, further comprising:
    using the computing device executing the machine learning engine, determining characterizations of the plurality of work tasks performed by the plurality of human actors including a time required for each of the plurality of human actors to perform each of the plurality of work tasks; and
    using the computing device, further determining the work task assignments based on the determined characterizations.

5. The method of claim 1, further comprising:
    using the computing device executing the machine learning engine, determining characterizations of the plurality of work tasks performed by the plurality of human actors including one or more of ergonomics of each of the plurality of human actors performing the plurality of work tasks, a skill level of one or more of the plurality of human actors used to perform one or more of the plurality of work tasks, and a time required for each of the plurality of human actors to perform each of the plurality of work tasks; and
    using the computing device, determining a certification expertise indicating that a given one of the plurality human actors is certified to a standard based on the determined characterizations.

6. The method of claim 1, further comprising, using the computing device executing the machine learning engine, further determining the one or more cycles, one or more processes, one or more actions, one or more sequences, one or more objects and one or more parameters from thermal sensor data.

7. The method of claim 1, further comprising, using the computing device executing the machine learning engine, further determining the one or more cycles, one or more processes, one or more actions, one or more sequences, one or more objects and one or more parameters from force sensor data.

8. The method of claim 1, further comprising, using the computing device executing the machine learning engine, further determining the one or more cycles, one or more processes, one or more actions, one or more sequences, one or more objects and one or more parameters from audio sensor data.

9. The method of claim 1, further comprising, using the computing device executing the machine learning engine, further determining the one or more cycles, one or more processes, one or more actions, one or more sequences, one or more objects and one or more parameters from light sensor data.

10. The method of claim 1, further comprising controlling one or more robot actors according to other corresponding ones of the work task assignments for the performance of further cycles of the plurality of work tasks.

11. A computer implemented method of determining work task assignments within an automated production line, the method comprising:
  receiving a sensor stream at a computing device, the sensor stream comprising sensor information obtained from one or more sensors at a plurality of manufacturing stations across an assembly line;
  using the computing device executing a machine learning engine to determine one or more cycles one or more processes, one or more actions, one or more sequences, one or more objects and one or more parameters and a plurality of actors by convolution neural network deep learning from the sensor stream, the convolution neural network comprising:
    a frame feature extractor configured to perform a two-dimensional convolution operation on the sensor stream and generate a two-dimensional array of feature vectors;
    an RoI detector unit configured to combine neighboring ones of the feature vectors to determine a dynamic region of interest, wherein the RoI detector unit and the frame feature extractor share layers of the convolution neural network; and
    an RoI pooling unit configured to extract a fixed-sized feature vector from an area of the dynamic region of interest and discard the remaining feature vectors of the sensor stream, wherein the convolution neural network analyzes actions within the dynamic region of interest without analyzing the feature vectors outside the dynamic region of interest;
  receiving with the computing device an identity of each of the plurality of actors identified within the sensor stream;
  using the computing device executing the machine learning engine to identify a plurality of work tasks within the sensor stream that are performed by each of the plurality of actors based on the determined one or more cycles, one or more processes, one or more actions, one or more sequences, one or more objects and one or more parameters;
  using the computing device to store, in a data structure, the sensor stream, the plurality of work tasks, and the plurality of actors;
  using the computing device to map respective work tasks performed by each of the plurality of actors to the sensor stream;
  using the computing device executing the machine learning engine to determine characterizations of the respective work tasks identified from the sensor stream performed by each of the plurality of actors including distribution functions that reflect variations in one or more of the plurality of work tasks;
  using the computing device to determine work task assignments which assign respective actors of the plurality of actors to perform respective work tasks of the plurality of work tasks during further cycles of the plurality of work tasks based on the characterizations of the plurality of work tasks for the plurality of actors;
  outputting corresponding work task assignments;
  using the computing device executing the machine learning engine to identify changes of one or more of the plurality of actors, the plurality of work tasks, and performance of the plurality of work tasks by the plurality of actors;
  using the computing device executing the machine learning engine, to update the work task assignments based on the changes of one or more of the plurality of actors, the plurality of work tasks, and performance of the plurality of work tasks by the plurality of actors; and
  outputting the updated work task assignments.

12. The method of claim 11, wherein the determined characterizations further include ergonomics of each of the plurality of actors used to perform the work tasks.

13. The method of claim 11, wherein the determined characterizations further include a skill level of each of the plurality of actors used to perform the work tasks.

14. The method of claim 11, wherein the determined characterizations further include a time required for each of the plurality of actors to perform the work tasks.

15. The method of claim 11, further comprising: using the determined characterizations to determine when one or more of the plurality of actors are certified to a standard.

16. The method of claim 11, wherein the sensor stream includes one or more of video frames, thermal sensor data, force sensor data, audio sensor data, and light sensor data.

17. A system comprising:
  a processor coupled to a bus;
  one or more sensors in communication with the bus and operable to sense progress of a plurality of work tasks at one or more stations; and
  a memory coupled to the bus and comprising instructions of a machine learning engine that when executed by the processor cause the system to implement a method of automatically determining work task assignments, the method comprising:
    the processor executing the machine learning engine to determine one or more cycles, one or more processes, one or more actions, one or more sequences, one or more objects and one or more parameters of a manufacturing operation of a product and a plurality of actors by convolution neural network deep learning from one or more video streams of the one or more sensors, wherein the machine learning engine determines the one or more cycles, one or more processes, one or more actions, one or more sequences, one or more objects and one or more parameters and the plurality of actors by:
      generating a two-dimensional array of feature vectors by performing a two-dimensional convolution operation on the one or more video streams with a frame extractor;
      determining a dynamic region of interest in the array of feature vectors with a RoI detector unit, wherein the convolution neural network comprises convolution layers shared by the frame extractor and the RoI detector unit;
      extracting a fixed-sized feature vector from an area within the dynamic region of interest; and
      analyzing actions within the fixed-sized feature vector while discarding areas of the one or more video streams outside the fixed-sized feature vector;
    the processor executing the machine learning engine to identify a plurality of work tasks performed by the plurality of actors at the one or more stations based on the one or more cycles, one or more processes, one or more actions, one or more sequences, one or more objects and one or more parameters and the plurality of actors determined from the one or more sensors;

the processor executing the machine learning engine to determine work task assignments of the identified plurality of work tasks for the plurality of actors;

outputting the work task assignments;

the processor executing the machine learning engine to identify changes of one or more of the plurality of actors, the plurality of work tasks, and performance of the plurality of work tasks by the plurality of actors, in real time;

the processor executing the machine learning engine to update the work task assignments based on the identified changes of one or more of the plurality of actors, the plurality of work tasks, and performance of the plurality of work tasks by the plurality of actors; and outputting the updated work task assignments.

18. The system of claim 17, further comprising:

using the processor executing the machine learning engine, to determine characterizations of the plurality of work tasks performed by the plurality of actors including ergonomics of the plurality of actors used to perform one or more of the identified plurality of work tasks; and using the processor executing, to further determine the work task assignments based on the determined characterizations.

19. The system of claim 17, further comprising:

using the processor executing the machine learning engine, to determine characterizations of the plurality of work tasks performed by the plurality of actors including a skill level of the plurality of actors used to perform one or more of the identified plurality of work tasks; and using the processor, to further determine the work task assignments based on the determined characterizations.

20. The system of claim 17, further comprising:

using the processor executing the machine learning engine, to determine characterizations of the plurality of work tasks performed by the plurality of actors including a time required for the plurality of actors to perform one or more of the identified plurality of work tasks; and using the processor, to further determine the work task assignments based on the determined characterizations.

21. The system of claim 17, further comprising:

using the processor executing the machine learning engine, to determine characterizations of the plurality of work tasks performed by the plurality of actors including one or more of ergonomics of each of the plurality of actors performing the plurality of work tasks, a skill level of each of the plurality of actors used to perform one or more of the plurality of work tasks, and a time required for each of the plurality of actors to perform each of the plurality of work tasks; and using the processor to determine a certification expertise indicating that one or more of the plurality of actors are certified to a standard based on the determined characterizations.

22. The system of claim 17, wherein the one or more sensors comprise one of: a video sensor, a thermal sensor, a force sensor, an audio sensor, and a light sensor.

* * * * *